US008529834B2

(12) United States Patent
Johns

(10) Patent No.: US 8,529,834 B2
(45) Date of Patent: Sep. 10, 2013

(54) BLOOD/AIR MASS EXCHANGE APPARATUS

(75) Inventor: Richard William Johns, Reading (GB)

(73) Assignee: Haemair Ltd. (GB)

(*) Notice: Subject to any disclaimer, the term of this patent is extended or adjusted under 35 U.S.C. 154(b) by 0 days.

(21) Appl. No.: 12/249,654

(22) Filed: Oct. 10, 2008

(65) Prior Publication Data
US 2009/0081079 A1  Mar. 26, 2009

Related U.S. Application Data

(63) Continuation of application No. PCT/GB2007/050114, filed on Apr. 13, 2006.

(30) Foreign Application Priority Data

Apr. 13, 2006 (GB) .................................. 0607410.8

(51) Int. Cl.
A61M 1/16 (2006.01)
A61B 5/08 (2006.01)
A61B 5/024 (2006.01)
A61B 5/145 (2006.01)

(52) U.S. Cl.
USPC ............. 422/46; 422/44; 422/45; 422/48; 604/6.14; 604/45; 604/158

(58) Field of Classification Search
USPC ............. 422/44, 45, 46; 604/6.14, 45, 158; 210/321, 72
See application file for complete search history.

(56) References Cited

U.S. PATENT DOCUMENTS

| | | | | |
|---|---|---|---|---|
| 3,743,097 A * | 7/1973 | Sausse | ................ | 210/321.75 |
| 3,927,981 A * | 12/1975 | Viannay et al. | ................ | 422/48 |
| 4,568,327 A * | 2/1986 | Seufert | ................ | 604/5.01 |
| 4,619,643 A * | 10/1986 | Bai | ................ | 604/43 |
| 4,975,247 A * | 12/1990 | Badolato et al. | ................ | 422/48 |
| 5,103,814 A * | 4/1992 | Maher | ................ | 128/204.18 |
| 5,601,714 A * | 2/1997 | Haveland | ................ | 210/436 |
| 5,609,632 A * | 3/1997 | Elgas | ................ | 128/898 |
| 5,695,717 A * | 12/1997 | Polaschegg et al. | ................ | 422/48 |
| 5,797,869 A * | 8/1998 | Martin et al. | ................ | 604/43 |
| 5,810,759 A * | 9/1998 | Merz | ................ | 604/6.11 |
| 6,004,511 A * | 12/1999 | Biscegli | ................ | 422/45 |
| 6,041,777 A * | 3/2000 | Faithfull et al. | ................ | 128/200.24 |
| 6,180,058 B1 * | 1/2001 | Lindsay | ................ | 422/44 |
| 6,642,045 B1 * | 11/2003 | Brasile | ................ | 435/284.1 |
| 6,709,418 B1 * | 3/2004 | Aboul-Hosn et al. | ................ | 604/158 |
| 2002/0143397 A1 * | 10/2002 | von Segesser | ................ | 623/9 |
| 2003/0131844 A1 * | 7/2003 | Kumar et al. | ................ | 128/200.24 |
| 2004/0052681 A1 * | 3/2004 | Mortensen et al. | ................ | 422/45 |
| 2004/0144383 A1 * | 7/2004 | Thomas et al. | ................ | 128/204.18 |
| 2005/0084416 A1 * | 4/2005 | Thomas | ................ | 422/45 |

* cited by examiner

Primary Examiner — Adam Marcetich
(74) Attorney, Agent, or Firm — GrayRobinson, P.A.; Michael J. Colitz, III

(57) ABSTRACT

There is provided a mass exchange apparatus (114) for use in blood/air mass exchange comprising plural blood flow conduits for defining a blood flow from a blood flow inlet provided thereto; and plural air flow conduits for defining an air flow from an air flow inlet provided thereto. The plural air flow conduits and plural blood flow conduits at least partially comprise gas-permeable membrane material, and the conduits are arranged relative to each other such as to enable transfer of oxygen from the air flow to the blood flow and transfer of carbon dioxide from the blood flow to the air flow through the membrane material.

62 Claims, 9 Drawing Sheets

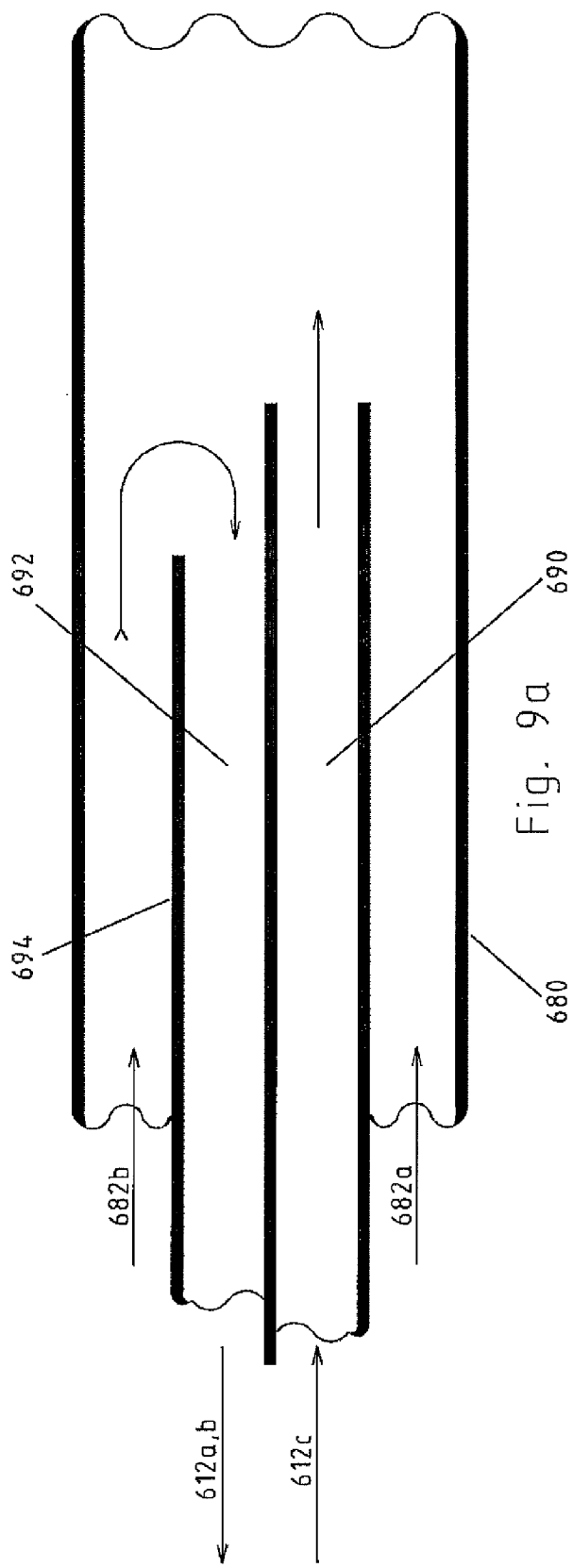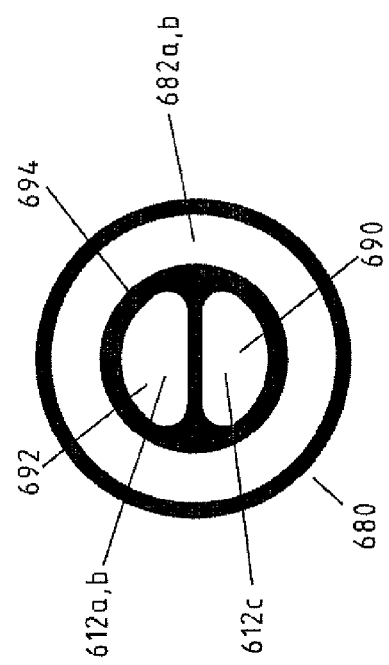
Fig. 9a
Fig. 9b

BLOOD/AIR MASS EXCHANGE APPARATUS

PRIORITY DATA

This application is a continuation of and claims priority under 35 U.S.C. §371 to International Application No. PCT/GB2007/050114 filed on Mar. 8, 2007, which claims priority from GB 0607410.8 filed on Apr. 13, 2006. The contents of both aforementioned applications are incorporated herein by reference.

TECHNICAL FIELD

The present invention relates to a compact blood/air mass exchange apparatus for use with an external or part-external respiratory aid.

BACKGROUND TO THE INVENTION

In Europe and North America, there are currently about 10,000 people on lung-transplant waiting lists. Each year, about 2500 people are transplanted, of whom approximately 2000 survive to live healthy lives. Each year about 2500 die on the waiting list, during a typical 2-year waiting period. The situation is actually far worse than the statistics would indicate because a much larger number of people are never entered onto waiting lists. These people may be excluded because they have no chance of surviving the wait for a transplant or because they are too old. There is little prospect that the situation will improve because the availability of donor organs is declining. The availability of suitable prosthetic lungs would revolutionize the situation. However, to date the development of prosthetic lungs has been deterred because of the perceived difficulty involved in reproducing the structure and function of a human lung. In addition to such deaths from chronic lung conditions, there are millions of deaths from acute conditions. For example, the WHO quotes nearly 4 million deaths per annum for Acute Respiratory Infection. In principle, a large proportion of these people have recoverable conditions and a device that directly oxygenated blood for a limited period would enable these people to recover.

The Applicant has now developed an improved blood/air mass exchange apparatus that is amenable for use as part of an external or intermediate respiratory aid for use by a patient with impaired lung function. Applicant's earlier published PCT Patent Application No. WO2005/118025 describes a mass exchange apparatus that functions as a counter-diffusion device to transfer oxygen from the air into the blood and carbon dioxide from the blood to the air. The blood and air flow in alternate channels or conduits. The walls defining the channels or conduits are gas-permeable to allow the required mass transfer. Applicant has now devised various improvements relating to the control of such a mass exchange apparatus. The improvements provide for more stability in use, and hence enhanced patient treatment.

The present application describes blood oxygenation using a membrane mass exchange apparatus that provides stable control of respiration for a conscious mobile patient. It addresses the specific problem that both the oxygen and carbon dioxide concentrations in the blood must be controlled. It recognizes that the body has its own internal control mechanisms based primarily on sensing blood carbon dioxide concentration and that no external controller has access to the natural biological set point. It further recognizes that within a membrane mass exchange apparatus the mass transfer coefficient for carbon dioxide may be an order of magnitude greater than that for oxygen. It consequently addresses the overall problem of providing a stable system suitable for use with a conscious mobile patient.

It is an object of the present invention to provide an improved mass exchange apparatus for use in blood/air mass exchange. It is also an object of the present invention to provide an improved external respiratory aid for use external to a human body. It is a further object of the present invention to provide an improved intermediate respiratory aid for use part internal to a human body and part external thereto.

SUMMARY OF THE INVENTION

According to a first aspect of the present invention there is provided a mass exchange apparatus for use in blood/air mass exchange comprising
(a) plural blood flow conduits for defining a blood flow from a blood flow inlet provided thereto; and
(b) plural air flow conduits for defining an air flow from an air flow inlet provided thereto;
wherein said plural air flow conduits and said plural blood flow conduits at least partially comprise gas-permeable membrane material, and the conduits are arranged relative to each other such as to enable transfer of oxygen from said air flow to said blood flow and transfer of carbon dioxide from said blood flow to the air flow through said membrane material,
and wherein said apparatus additionally comprises
(c) a sensor for sensing patient respiratory demand; and
(d) a controller for controlling the rate of blood/air mass exchange by separate control of the levels of carbon dioxide and oxygen in the air flow responsive to the sensing of patient respiratory demand by the sensor.

The mass exchange apparatus herein, is suitable for use in blood/air mass exchange. Within the mass exchange apparatus, the blood and air do not directly come into contact.

The mass exchange apparatus herein, comprises plural blood flow conduits for defining a blood flow. That blood flow is from a blood flow inlet to a blood flow outlet provided to the apparatus (i.e. the blood flows from blood flow inlet through the plural blood flow conduits to the blood flow outlet). Embodiments are also envisaged in which plural blood flow inlets and/or plural blood flow outlets are employed in any suitable arrangement or configuration.

The mass exchange apparatus herein, comprises plural air flow conduits for defining an air flow. The term "air" herein is defined to mean any fluid mixture or solution containing oxygen and carbon dioxide, and the term "air flow" is used herein to mean a flow of any such fluid mixture or solution containing oxygen and carbon dioxide.

The air flow in the plural air flow conduits is from an air flow inlet to an air flow outlet provided to the apparatus (i.e. the air flows from air flow inlet through the plural air flow conduits to the air flow outlet). Embodiments are also envisaged in which plural air flow inlets and/or air flow outlets are employed in any suitable arrangement or configuration.

The plural air flow conduits and plural blood flow conduits at least partially comprise gas-permeable membrane material. The conduits are arranged relative to each other such as to enable transfer of oxygen from said air flow to the blood and transfer of carbon dioxide from the blood flow to the air flow through the membrane material.

It will be appreciated that the walls defining the blood flow and air flow conduits may be separately formed and arranged relative to each other to enable the necessary exchange of air (oxygen) and carbon dioxide. In one aspect, the blood and air flow conduits share at least some common walls, again with the arrangement selected to enable the necessary exchange of air (oxygen) and carbon dioxide.

The plural blood flow conduits and plural air flow conduits may take the form of tubes or closely-spaced plates. Suitably, where one phase flows through the tubes, the other phase may flow through the space between the tubes.

Suitably, the blood flow conduits and/or air flow conduits have a diameter (or cross-section of non-circular conduit) and/or spacing of less than 0.5 mm.

The gas-permeable membrane materials for the walls defining the blood and air flow conduits may comprise conventional materials (e.g. polymers) or composite materials. A composite material may comprise of two components, a first material component of the composite provides physical strength and a second material component provides gas permeability.

Suitable gas-permeable membrane materials for the walls are biocompatible in nature.

By way of background it is noted that the design of the mass exchange apparatus herein is suitably arranged to minimize the possibility of the generation of blood clots, which might risk the life of the patient. The natural behaviour of blood is to clot when it contacts any surface other than it expects to contact naturally within the body. Specifically, it does not normally clot within blood vessels. This clotting behaviour is essential to avoid haemorrhage whenever there is a cut or bruise. Biocompatible materials for use in the mass exchange apparatus herein desirably achieve biocompatibility by presenting a suitable surface to the blood. Not only are the gas-permeable membrane materials herein suitably biocompatible, but also the tubing connecting the patient with the apparatus and any blood pumps and valves. Preferably, all valves are in contact only with air (or the oxygen and carbon dioxide containing fluid used instead of air).

In aspects, the mass exchange apparatus herein can be made from any materials widely used in medicine. The patient would take anti-coagulant medication to avoid clots forming. However, use of anticoagulants presents a risk of haemorrhage. Hence, it is desirable to employ materials such that, even in the absence of anticoagulants, blood clots do not form in the mass exchange apparatus. The incentive to employ such anti-clotting materials is particularly important in such an apparatus intended for medium to long-term use. Generally, the anti-clotting property is introduced by applying a coating to surfaces that contact blood. In aspects, the gas-permeable membrane materials herein are subjected to suitable surface treatment thereof.

In one aspect, the gas-permeable membrane materials present an inert surface that result in minimal interaction with the blood. Suitable inert materials can be hydrophilic or hydrophobic, can have a surface that tightly binds water, or can have a surface that mimics the endothelial cells coating the inside of natural blood vessels.

In another aspect, the gas-permeable membrane materials incorporate an anti-thrombogenic agent (or agents) in their surface. Materials that incorporate anti-thrombogenic agents most frequently have heparin (or a heparin derivative) bound to the surface. Heparin may suitably be bound covalently or ionically.

In a further aspect, the gas-permeable membrane materials discharge small amounts of anti-thrombogenic agent from their structure. Materials that discharge anti-thrombogenic agents include materials that release heparin and materials that release nitric oxide (NO). Generally, these materials require a surface coating that is too thick for use for the membranes in the mass exchange apparatus. However, they might be useful for other parts of the respiratory aid apparatus. Recent developments include thin surface-active coatings that generate nitric oxide from the biological materials in contact with the surface. For example, they can produce a small flux of nitric oxide when in contact with blood.

Also envisaged are gas-permeable membrane materials that combine two or more of the above properties.

Some surface treatments bind preferentially to specific substrates. Thus, in order to obtain the desired anti-coagulant surface, the choice of (substrate) membrane materials may be limited. Conversely, in order to obtain the desired diffusive properties, the choice of base materials may be limited. It is desirable to achieve an optimal compromise between diffusive and anti-coagulant properties for the membrane materials.

Together with high diffusivity and good blood compatibility, the membrane materials desirably exhibit adequate physical strength. Highly diffusive materials tend to be soft. Thus, in one aspect there is employed a thin layer of diffusive material backed by a strong mesh or microporous material. The strong mesh might be provided by an aramid fibre (for example, the product Kevlar, manufactured and sold by Dupont Inc) or by Carbon fibre.

Particular gas-permeable membrane materials for the walls include those described in European Patent Application No. 1,297,855 in the name of Dainippon Ink & Chemicals. Thus, the materials suitably comprise a hollow fibre membrane comprising poly-4-methylpentene-1 and having an oxygen permeation rate $Q(O_2)$ at 25° C. of from $1 \times 10^{-6}$ to $3 \times 10^{-3}$ $(cm^3(STP)/cm^2.sec.cmHg)$ and an ethanol flux of from 0.1 to 100 ml/min.m$^2$, wherein said membrane has (e.g. in the side of the blood flow) a surface comprising an ionic complex derived from:

quaternary aliphatic alkylammonium salts; and
heparin or a heparin derivative, and
wherein said quaternary alkylammonium salts comprise a
 quaternary aliphatic alkylammonium salt having from 22
 to 26 carbon atoms in total and a quaternary aliphatic
 alkylammonium salt having from 37 to 40 carbon atoms in
 total.

Suitably, the quaternary alkylammonium salt comprises from 5 to 35% by weight of a quaternary aliphatic alkylammonium salt having from 22 to 26 carbon atoms in total and from 65 to 95% by weight of a quaternary aliphatic alkylammonium salt having from 37 to 40 carbon atoms in total.

Suitably, the quaternary aliphatic alkylammonium salt comprises a dimethyldidodecylammonium salt or a dimethyldioctadecylammonium salt.

The apparatus additionally comprises at least one sensor for sensing patient respiratory demand, which typically means patient demand for oxygen. The sensor typically senses a parameter related to patient respiratory demand.

In aspects, the mass exchange apparatus comprises plural sensors, each for sensing patient respiratory demand. Suitably, each of said plural sensors senses a different parameter related to patient respiratory demand. In aspects, an online computer controller can then combine the various parameters and employ a formula or algorithm for determining the patient respiratory demand.

In one aspect, the sensor detects the pulse rate of a patient, which indicates patient respiratory demand for oxygen. In other aspects, the sensor detects the breathing rate of the patient and/or the blood circulation rate and/or the oxygen concentration in the venous blood and/or the strength of the pulse of the patient, each of which is indicative of the patient respiratory demand for oxygen. In other aspects, the sensor senses blood oxygen saturation, which may vary in return venous blood flow to show higher oxygen usage in the body without a proportional increase in pulse rate or blood circulation rate.

The apparatus further comprises a controller for controlling the rate of blood/air mass exchange by separate control of the levels of carbon dioxide and oxygen in the air flow responsive to the sensing of patient respiratory demand by the or each sensor.

Preferably, the or each sensor communicates with the controller by suitable communication means. The or each sensor is typically, an electronic sensor and communication with the controller is typically via wired or wireless electronic transmission means.

Preferably, the controller separately controls the level of carbon dioxide and oxygen in the air flow at the air flow inlet. The objective of the control may be to set desirable levels for both blood oxygen and blood carbon dioxide. Alternatively, the objective of the control may be primarily to reduce blood carbon dioxide levels so that residual lung function provides the required blood oxygenation. In a preferred aspect, the controller therefore acts at the air flow inlet to control carbon dioxide and oxygen levels thereat.

Suitably, in the mass exchange apparatus herein, the air and blood flows are arranged such as to provide blood oxygen/carbon dioxide relationships similar to those for natural respiration.

In one aspect, the air flow pattern is a combination of counter-current to the blood flow and co-current to the blood flow and may include recycled air flow. In another aspect, the air flow is mainly counter-current (i.e. in the opposite flow sense) to the blood flow. In another aspect the air flow is mainly at right angles to the blood flow (cross-current flow). In another aspect, there may be plural air or blood inlets providing air flow at an angle to the blood flow (mixed flow mass exchange).

The blood/air mass exchange apparatus effectively acts as a counter-diffusion device that functions to transfer oxygen from the air into the blood and carbon dioxide from the blood to the air. In one aspect of the mass exchange apparatus, blood and air flow in alternate channels between a series of plates that are separated by a small distance. Suitably, the spacing between the plates is less than 0.5 millimeters, preferably from 0.2 to 0.05 millimeters.

The plates are gas-permeable membranes allowing oxygen and carbon dioxide to diffuse in opposite directions. Alternative arrangements with channels or tubes of various cross-sections are possible. The blood flows in a first direction through the apparatus. Air may flow in alternate directions (as in normal breathing); counter-current to the airflow; intermittently counter-current; co-current or intermittently co-current to the airflow. Alternative flow patterns are possible in which the blood and air flow in relative directions which can be adjusted from 0° to 180°.

The total mass-exchange area is a fraction of the area found in a living human lung. Thus, it is expected to be of the order of from 1 to 25 square meters, for example about 10 square meters compared to 70 square meters that is typically found in a human lung. Where an air feed is provided to the apparatus, the mass exchange area is likely to be towards the top end of this range such as from 15 to 25 square meters. Where an oxygen/nitrogen feed is provided to the apparatus, the mass exchange area may be towards the lower end of the range such as from 1 to 5 square meters.

In another aspect, the mass exchange apparatus herein may be used primarily to reduce blood carbon dioxide concentration. With a lower blood carbon dioxide concentration, oxygen is more soluble in blood. Thus, with lower carbon dioxide in the entering blood, lungs with a reduced capacity might be able to augment the oxygen added in the mass exchange apparatus. In such applications, mass exchange areas as low as one square meter might be effective. In this aspect, the feed may be air or a mixture of oxygen, carbon dioxide and an inert fluid.

In more detail, it is believed that for oxygenation, a mass exchange area of from 2 to 25 square meters is most suitable, whereas for carbon dioxide removal, a mass exchange area of from 1 to 5 square meters is most suitable.

Where more than one mass exchange apparatus herein, are used together the total mass exchange area is divided between the apparatus (e.g. where two apparatus are used in tandem, the total mass exchange area provided by these two in combination should be from 1 to 25 square meters).

A total mass-exchange area of from 1 to 25 square meters is a multiple of the area conventionally found in blood oxygenators used as part of heart/lung devices for thoracic surgery. Such blood oxygenators typically provide less than one square meter of surface area. It is also a multiple of the area typically employed in Extracorporeal Life Support (ECLS) apparatus, which is typically around 1 square meter. The apparatus herein typically employs a larger area because it employs air (giving a lower mass transfer driving force) instead of oxygen, and is intended for medium to long-term use (days to years) by a conscious, mobile patient. Natural air is employed to give light weight and mobility rather than requiring the use of enhanced oxygen concentrations that require an oxygen supply (e.g. provided as a weighty oxygen cylinder). Blood oxygenators use oxygen as the gas phase. They are normally used over limited periods (of hours) with unconscious patients with low metabolic rates, often at lowered temperatures to reduce metabolic rates further. ECLS blood oxygenators also use oxygen as the gas phase and are used for periods from a day up to about 1 month.

There is also provided use of the mass exchange apparatus herein with a synthetic gas supply consisting of oxygen, carbon dioxide and an inert gas, such as nitrogen. Additionally, there is provided use of an oxygen-rich liquid supply consisting of oxygen, carbon dioxide and an inert liquid in which the gases are soluble (for example, a perfluorocarbon). In order to provide the required level of control, these supplies all contain less than 100% oxygen. Hence, they have a reduced driving force for mass transfer, which necessitates a larger area than conventionally employed in ECLS blood oxygenator devices. Where an inert fluid other than nitrogen is employed, a second mass exchange apparatus will be required to remove carbon dioxide from the fluid so that it may be recycled.

In aspects, the mass exchange apparatus additionally comprises an air recycle loop, and wherein the air flow inlet receives both a primary air flow feed and a recycled air flow feed from said air recycle loop. Such an air recycle loop is primarily used for an air feed. There is less advantage in the use of a recycle loop when using a synthetic gas (or fluid) feed where the right proportions are simply fed into the air flow inlet.

In aspects, the controller acts to control the relative proportions of primary air flow feed and recycled air flow feed received at the air flow inlet.

In aspects, the controller acts to control the recycle rate of the air recycle loop.

In aspects, the controller acts to control the relative feed rate of the primary air flow feed and recycled air flow feed.

In aspects, the air flow inlet receives plural fluid flow feeds selected from the group consisting of an inert fluid (e.g. nitrogen) feed, an oxygen feed, a carbon dioxide feed and an air feed.

In aspects, the air flow inlet receives three fluid flow feeds comprising an inert fluid (e.g. nitrogen) feed, an oxygen feed and a carbon dioxide feed.

In aspects, the air flow inlet receives two or three fluid flow feeds, each of which contains one or more of the components oxygen, carbon dioxide and an inert fluid.

In aspects, the controller acts to control the relative proportions of each of the plural fluid flow feeds received at the air flow inlet.

In aspects, the controller acts to control the relative flow rates of each of the plural air flow feeds received at the air flow inlet.

In aspects, the mass exchange apparatus contains a secondary mass exchange apparatus to extract carbon dioxide and replenish oxygen in the exhaust from the mass exchange apparatus. The replenished exhaust may then be recycled to the mass exchange apparatus. The secondary mass exchange apparatus may optionally be fed with a recycled air feed in order to control the proportions of oxygen and carbon dioxide in the synthetic fluid mixture fed to the mass exchange apparatus. This kind of arrangement is most suitable for use with an inert fluid feed other than nitrogen. In particular, if an expensive inert fluid, such as perfluorocarbon, is employed it would make sense not to exhaust it to atmosphere. If an inert gas such as helium or argon were employed, it would also be desirable to reuse it.

In one aspect, the mass exchange apparatus of the present invention is incorporated into an external respiratory aid to augment lung function comprising the mass exchange apparatus and auxiliary equipment to pump air and blood through the device.

Thus, according to another aspect of the present invention there is provided a respiratory aid apparatus for external connection to a patient comprising (a) at least one mass exchange apparatus as described herein; (b) an air pump for pumping air through said air conduits; and (c) a blood pump for pumping blood through said blood conduits.

Suitably, the respiratory aid apparatus comprises two mass exchange apparatus arranged in parallel fashion. This arrangement has benefits including the facility to replace one mass exchange apparatus whilst the other is still operational (e.g. still functioning).

The external respiratory aid apparatus suitably incorporates tubing to extract oxygen-depleted, high carbon dioxide, blood from the patient and return oxygenated blood, with low carbon dioxide. Separate tubes may extract the blood and return it. Alternatively, the extraction and return tubes may be joined concentrically to simplify fitting the device and to extract and return blood from adjacent positions (for example, in the vena cava system). In this way, no vein or artery would suffer depleted blood flow. Particularly, the heart would experience a full flow of oxygenated blood.

In one use aspect, the external respiratory aid is arranged to allow the option of blood extraction and return through a single entry point in a vein of a patient. Thus, input tubing to the blood pump is arranged to provide blood extraction and return via the desired single entry point. This mode of use simplifies the clinical procedure.

Suitably, the external respiratory aid apparatus is provided with short connecting lines (e.g. tubes of length less than 1 meter, preferably less than 0.5 meters) for connecting to the patient to provide the desired air and blood flows. Short connecting lines are preferred because heat loss is thereby minimized, thus reducing any risk of hypothermia. Alternatively heated lines may be employed (e.g. using heat exchange with the body), but this approach adds complexity.

Suitably, the respiratory aid apparatus is arranged such that extracted blood undergoes counter-current heat transfer with returned blood. This arrangement desirably minimizes any temperature fall in the blood extracted from the body and returned after mass exchange.

Suitably, the respiratory aid apparatus additionally comprises an air filter for filtering the air. A HEPA filter is an example of a suitable air filter.

Optionally, where it is desired to minimize the loss of water vapour from the patient, the respiratory aid apparatus additionally comprises a humidifier for humidifying the air. Optimally, humidified air is directed to the mass exchange apparatus at near blood temperature.

Suitably, the respiratory aid apparatus additionally comprises a heat exchange apparatus. Suitably, the air flow is arranged to pass through a heat exchange apparatus that uses body-heat to pre-heat the air to near body-temperature. The heat exchange apparatus may consist of one or more flexible tubes or conduits that are arranged into a sheet that is placed against the body of a patient and insulated on the side away from the body of a patient. Alternatively, or additionally, the incoming air may undergo heat exchange with the exhaust air.

In a further aspect, the mass exchange apparatus of the present invention is incorporated into an intermediate respiratory aid for placing inside the body of a patient (without removing the lungs), such that the blood is pumped through the mass exchange apparatus by the natural circulatory system (ultimately the heart) of the patient. The air supply is suitably, external. The mass exchange apparatus is suitably arranged to connect directly to a vein, for example of the vena cava system, of a patient. The intermediate respiratory aid eliminates the necessity for the blood pump of the external respiratory aid. The device could take all, or part of the blood flow. The air would be pumped from outside the body, as for the external respiratory aid. As for the external respiratory aid, the flow pattern and relative flow rates would suitably be adjusted such that the natural carbon dioxide/oxygen relationship was mimicked. Desirably, located outside the body of a patient, there is a HEPA filter between the pump and the entry point of the tube into the body. The air exhaust from the mass exchange apparatus is conducted outside the body, where it is discharged to atmosphere. Alternatively, before discharge, it may undergo counter-current heat exchange with the incoming air to minimize heat losses.

Thus, according to another aspect of the present invention there is provided an intermediate respiratory aid apparatus for internal connection to a patient comprising (a) at least one mass exchange apparatus as described herein; and (b) an air pump for pumping air through said air conduits.

The external respiratory aid and intermediate respiratory aid both have a distinct purpose compared to a heart/lung machine or an ECLS device in that they are intended for long term connection to a patient who is conscious and mobile. To achieve this goal, they are designed to be robust, lightweight and portable.

The Applicant has appreciated that counter-current air flow might be employed to maximize mass transfer rates in a mass exchange apparatus of a given area. However, counter-current flow disproportionately increases the efficiency of carbon dioxide mass transfer. Accordingly, co-current flow and recycle may be included to match the natural carbon dioxide/oxygen relationship in the blood. In this way, the body's natural respiratory control mechanisms operate normally.

Normal operation of the control mechanisms (primarily sensing carbon dioxide levels) has two benefits.

The first benefit is that the natural control mechanisms for the metabolic system as a whole operate normally and correctly. The second benefit is that any external controller can take advantage of natural responses (such as increased heart rate) to maintain correct blood oxygen and carbon dioxide levels without necessarily employing recourse to direct measurement of blood gas compositions.

Suitably, when the external respiratory aid apparatus takes only a fraction of the blood flow, mass transfer is maximized by employing counter-current air flow. When larger blood flows are taken, for example with the intermediate respiratory aid, air flow patterns including co-current and recycle flow may be employed to mimic natural oxygen/carbon dioxide relationships in the blood.

Control of Mass Exchange Apparatus

The present invention recognizes that it is possible to support life by oxygenating blood passing through a mass exchange apparatus inserted in the patient's blood circulation. Such mass exchange is required when the patient's lungs are ineffective. To date, such life support can be applied in limited circumstances. For example, it is routinely applied during thoracic surgery, when the patient is anaesthetized. It is also applied to patients who are largely immobilized and maintained in hospital intensive care (or similar) units. This invention is focused on application to conscious mobile patients. Such patients can be taken out of intensive care and, ultimately, cared for at home. Integration with the body's natural control mechanisms is of paramount importance for a conscious mobile patient. Inadequate control can lead to shut down of the respiratory system or to dangerously high heart rates. Any control system must recognize that oxygen demand (and carbon dioxide rejection) can vary by in excess of a factor of ten in normal conscious life.

The body uses blood carbon dioxide concentration as the primary stimulus to control the respiratory rate. If the blood carbon dioxide concentration is too high, respiration rate is increased to both lower the blood carbon dioxide concentration and increase the blood oxygen concentration. Conversely, if the blood carbon dioxide concentration is too low, the respiratory rate is decreased. Any external apparatus that sets the blood carbon dioxide concentration too low risks causing the respiratory system to shut down altogether. Such shut-down causes death. There are converse risks if an external apparatus sets the blood carbon dioxide level too high. The internal set points, by which the body senses whether concentrations are "too high" or "too low" are not known. Furthermore, they change with time. Hence, it is impossible for any external apparatus that directly controls carbon dioxide (or oxygen) concentration to set a level that guarantees stable respiration. Thus, an indirect control mechanism is suggested that senses the body's oxygen demand through measurement of patient respiratory demand. For example, pulse rate provides a measure of patient respiratory demand.

The control problem is exacerbated by the fact that, for membrane mass exchange apparatus, the mass transfer coefficient for carbon dioxide is more than an order of magnitude greater than it is for oxygen. In natural lungs, the ratio is approximately 2:1. Thus, simply replacing the function of natural lungs with a mass exchange apparatus would give excessively high carbon dioxide transfer leading to excessively low blood carbon dioxide concentrations. For this reason, in any membrane mass exchange apparatus, it is necessary to control oxygen and carbon dioxide concentrations separately.

Without active control, coupling a mass exchange apparatus to the respiratory system of a patient creates an intrinsically unstable system. Furthermore, conventional control, in which we attempt to control oxygen and carbon dioxide concentrations at pre-set levels, is also intrinsically unstable. The control system described herein allows the natural respiratory control system to operate without interference. There is recognition of the need for a progressive non-linear relationship between mass transfer rates and respiratory demand. At the same time, the relationship between blood carbon dioxide and oxygen concentrations must be similar to the natural relationship. Such a control system is both stable and simple.

Thus, it is not essential to measure blood oxygen and carbon dioxide concentrations; it is only necessary to sense a measure of respiratory demand (such as pulse rate). Measurement of venous blood oxygen concentration may facilitate a more sensitive control system.

Described herein, are two alternative ways of achieving the desired independent control of oxygen and carbon dioxide concentrations. In both cases, the total blood flow rate through the mass exchange apparatus is controlled to be an approximately constant proportion of the blood flow through the main veins. Also, in both cases, the gas phase passing through the mass exchange apparatus contains (at least) three components. It contains an inert gas (for example, nitrogen), oxygen and carbon dioxide. The driving force for oxygen mass transfer can be adjusted by controlling the gas-phase oxygen concentration. Similarly, the driving force for carbon dioxide mass transfer can be controlled by controlling the gas-phase carbon dioxide concentration. It may be necessary to alter the driving forces for each gas by at least a factor of five. Consequently, any apparatus employing just oxygen and carbon dioxide must fail. In order to reduce the gas-phase concentration of oxygen significantly below 100%, very high concentrations of carbon dioxide would be required. Such high concentrations of carbon dioxide would saturate the blood with carbon dioxide and cause death. The three components required can be provided with an air feed (giving oxygen and nitrogen) and carbon dioxide from a recycle from the mass exchange apparatus outlet. Alternatively, the three components could be provided by a separate feed of each pure gas. Intermediate cases are possible. For example, it is possible to employ an air feed together with a separate pure carbon dioxide gas feed.

In one aspect, air is used together with a recycle around the mass exchange apparatus. The concentrations of carbon dioxide and oxygen in the gas phase are controlled by adjusting both recycle rate and air feed rate. With low feed rate and high recycle ratio, carbon dioxide accumulates in the recycle stream. The high concentration in the gas stream gives a correspondingly high carbon dioxide concentration in the blood stream. Lower recycle rates and higher air feed rates give lower carbon dioxide concentrations and higher oxygen concentrations.

In another aspect, oxygen and carbon dioxide are added to an inert fluid, such as an inert gas (for example, nitrogen) stream. The concentrations are adjusted by adjusting the flow rates of the oxygen and carbon dioxide streams. In alternatives, a perfluorocarbon liquid is employed as the inert fluid. Where perfluorocarbon liquid is allowed to weep very slowly through the gas-permeable membrane it might suppress blood clotting.

It is recognized that for some patients with advanced lung disease, the usual natural control mechanism based on sensing carbon dioxide level is ineffective. The respiratory system for such patients is governed by low oxygen concentration. Suddenly presenting such patients with improved oxygen levels can induce sudden respiratory failure (hypoxic response). For such patients, a control system must gradually reduce carbon dioxide levels and improve oxygenation such that the body's natural control mechanism has time to recover.

The present invention aims to provide a control system that adjusts blood flow through a mass exchange apparatus (or other blood oxygenation device) in proportion to the blood flow rate through the heart and major veins.

The present invention further aims to provide a control system that adjusts both oxygen concentration and carbon dioxide concentration for a gas flowing through a mass exchange apparatus. The concentrations are adjusted so that mass transfer rates respond to respiratory demand (metabolic rate). The blood carbon dioxide concentration is such as to stimulate the body's own natural respiratory control mechanisms. This system could be applied equally to mass exchange apparatus that take the whole flow of blood in a vein and to mass exchange apparatus that take only a proportion of the flow.

The present invention further aims to provide a control system that achieves the desired inlet and outlet oxygen and carbon dioxide concentrations by adjusting a natural air feed and a recycle of exit gas from the mass exchange apparatus. The recycle serves the purpose of increasing carbon dioxide concentration in the inlet stream to the mass exchange apparatus.

The present invention further aims to provide a control system that adjusts the flow rate of three gas streams, an inert gas (for example nitrogen), oxygen, and carbon dioxide to achieve the required mixture concentrations.

The present invention further aims to provide a control system that adjusts the flow rate of three gas streams, each of which may be a mixture of an inert gas (for example nitrogen), oxygen, and carbon dioxide to achieve the required mixture concentrations.

The present invention further aims to provide a control system that adjusts the flow rate of two gas streams to achieve the required mixture concentrations. One of the gas streams is relatively lean in oxygen and rich in carbon dioxide. The other gas stream is relatively rich in oxygen and lean in carbon dioxide. The stream concentrations are chosen such that mixtures can achieve mass transfer rates required for all levels of activity from rest to maximum exertion.

The present invention further aims to provide a control system that adjusts the flow rate of natural air and of a synthetic gas mixture (for example comprising inert gas, oxygen and carbon dioxide) to achieve the required mixture concentrations with or without recycle from the mass exchange apparatus outlet.

The present invention further aims to provide a control system that employs heart rate to estimate respiratory demand.

The present invention further aims to provide a control system that employs heart rate together with other measures to estimate respiratory demand. Such other measures may include venous blood oxygen saturation at the inlet to the apparatus.

For patients in which, hypoxic response presents a risk, the present invention further aims to provide a control system that gradually brings a mass exchange apparatus (or other blood oxygenation device) into action using measures such as heart rate to minimize the risk of respiratory shut down.

External Respiratory Aid Apparatus

In the external respiratory aid apparatus aspect of the present invention, part of the oxygen-depleted blood in the veins approaching the heart of the patient is diverted and taken out of the body through a tube inserted in the blood vessel. The diverted blood is passed through an externally located mass exchange apparatus. The blood is returned to the main arteries leaving the heart. Alternative extraction and return points are possible. For example, the blood could be taken from the veins before the heart and returned to the veins at a later point, still before the heart. In this way, the heart does not have to work with depleted blood flow or deficient oxygen supply. A further benefit of this arrangement is that the extraction and return tubes could be joined to require only one entry point into the vein system. For example, the tubes could be concentric, with the return tube inside the extraction tube. The alternative of placing the extraction and return points between the heart and lungs would make the closest match to the performance of natural fully functioning lungs. However, the clinical operation to insert tubes at that point is more complex.

The heart itself would probably be incapable of driving a flow-divider that sent a proportion of the blood through the external respiratory aid. A peristaltic pump or other device designed not to damage the blood therefore typically pumps the extracted blood through the mass exchange apparatus. A small fan is suitably used to drive air through the mass exchange apparatus. Such an external respiratory aid is clearly heavier than a prosthetic lung because it requires a pump, a fan and a power source. The total device (mass exchange apparatus plus pump and power source) would weigh at least a fraction of a kilogram, and might weigh several kilograms. However, even at several kilograms it would still be sufficiently portable to enable to the patient to exercise and achieve a level of fitness that would not otherwise be possible.

Taking the blood flow outside the body to the external respiratory aid apparatus gives greater risk of infection and physical damage. The apparatus is also bulkier and more complex. However, there will be a range of applications in which an external respiratory aid is preferred. For example, the lung condition may be reversible (such as occurs with Acute Respiratory Infection). It would be counter-productive to divide a main vein or to remove a potentially healthy lung. In some circumstances the device might replace a heart-lung machine.

In normal applications, it is anticipated that only part of the blood supply will go through the mass exchange apparatus. This division is made because it leaves no blood vessels entirely devoid of flowing blood; and it leaves the normal mammalian control functions operational. Thus, if carbon-dioxide levels rise, the patient's heart and lungs will work harder. Unless lung function is completely lost, such action will reduce carbon dioxide and increase oxygen. In this way, the patient will avoid the confusion of a non-functioning respiratory control system. Preferably, blood flow is monitored and the blood and air flow though the external respiratory aid automatically adjusted according to rate. In this way, an approximately constant fraction of the blood flow would be diverted through the external respiratory aid, and desired blood oxygen and carbon dioxide concentrations achieved. This control action is important where the patient's own lungs are severely compromised. Without control, there is risk of extracting a flow greater than that in the relevant vein, resulting in damage through reverse flow in the vein. Furthermore, without control, the patient may sense a reversal of the normal physiological responses. Thus, as the heart beats faster, and the blood flow increases, the fixed flow of oxygenated blood from the external mass exchange apparatus would be diluted by a larger flow of non-oxygenated blood. The resulting mixed blood flow would have lower oxygen and higher carbon dioxide concentration. This response could confuse the patient's natural control system that expects oxygen levels to rise and carbon dioxide levels to fall when the heart beats faster and the patient breathes harder. Control (e.g. by means of a suitable sensor/controller) would restore the normal response to heart rate and breathing. The invention herein, includes the option of co-current air flow and/or recycle of part of the air through the external mass exchange apparatus. Use of co-current air flow and/or air recycle increases carbon dioxide concentration proportionately more than the decrease in oxygen concentration. Adjusting total air flow and recycle rates separately, enables the blood concentrations of carbon dioxide and oxygen to be independently adjusted. The required relationships are easily programmed into an automatic controller that only needs to sense one measure of metabolic oxygen demand.

The provision of an external respiratory aid that removes carbon dioxide from the blood may permit additional treatments. For example, a number of lung infections result from bacteria that are averse to high oxygen concentrations. In such a situation, there is no benefit in breathing higher levels of oxygen (for example, beyond 40%) because the defective lungs cannot get rid of the excess carbon dioxide. The provision of an external, auxiliary breathing-device would overcome this constraint. In this application, the main function of the device may be to reduce blood carbon dioxide concentration before the blood is returned upstream of the lungs.
Intermediate Respiratory Aid Apparatus.

For longer-term use, the external respiratory aid can be replaced by an intermediate system in which the mass exchange apparatus is within the body. The mass exchange apparatus takes the whole blood flow from a vein and returns the oxygenated blood flow to the vein. The intermediate system eliminates the necessity for a blood pump and is less vulnerable to damage.
Use Aspects The mass exchange apparatus and respiratory aid devices herein are suitable for use with a human or animal (particularly mammalian) subject. Installation and/or use are typically under the control of a physician or veterinary surgeon.

BRIEF DESCRIPTION OF THE DRAWINGS

The present invention will now be described further with reference to the accompanying drawings, in which:—

FIG. 9a shows a schematic representation of an alternative extraction/return system for the external respiratory aid herein; and FIG. 9b shows a cross-sectional view of the alternative extraction/return system of FIG. 9a.

Referring now to the drawings, FIG. 1 illustrates the core part of an air/blood mass exchange apparatus herein comprising plural blood flow conduits $10a$ to $10c$ for defining blood flow $12a$ to $12c$; and plural air flow conduits $20a$ to $20c$ for defining air flow $22a$ to $22c$. It may be seen that the blood $12a$-$c$ and air flow $22a$-$c$ is in alternate channels defined by a series of plates, tubes or conduits $30a$-$e$. The plate separation, tube diameter or conduit cross-sectional dimension should be less than 0.5 millimeters. Whilst for the purposes of representation, FIG. 1 shows a relatively small number of channels it will be appreciated that the actual mass exchange apparatus will comprise several thousand channels to give an overall mass transfer area of from 1 to 25 square meters.

The blood flows in a first direction $12a$-$c$ through the apparatus. As shown, the air flows in a second direction $22a$-$c$ counter to the first direction. In aspects, air may flow in alternate directions (as in normal breathing), counter-current to the air flow, or intermittently counter-current to the air flow. In alternatives, the air flow $22a$-$c$ may be co-current to the blood flow $12a$-$c$; or the air flow $22a$-$c$ may be at right angles to the blood flow $12a$-$c$ (cross-current flow); or the air flow $22a$-$c$ may be at an angle to the blood flow $12a$-$c$ (mixed flow). Cross current or mixed flow is possible when the fluid selected for cross flow does not flow within tubes or similar conduits. With a tubular mass exchanger, only one phase (that not in the tubes) can flow cross-current. With a plate mass exchanger, either phase can be cross-current.

Figure 1:
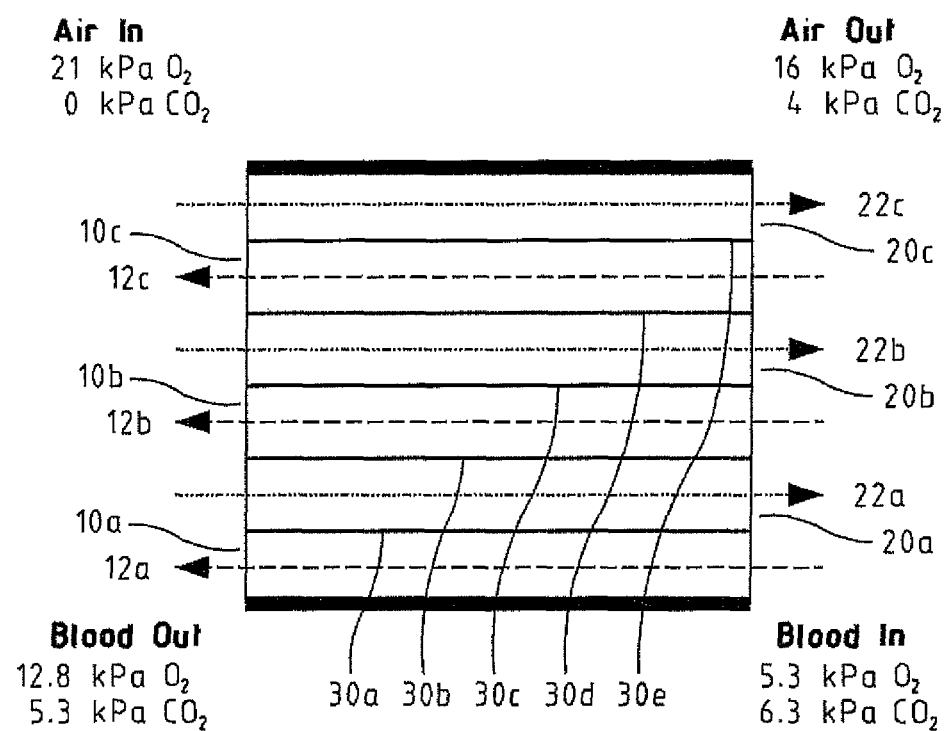
FIG. 1 shows a schematic representation of the blood and air flow conduits of an air/blood mass exchange apparatus herein.

The plates $30a$-$e$ are gas-permeable membranes that enable transfer of oxygen from the air to the blood and transfer of carbon dioxide from the blood to the air through said membrane material. FIG. 1 also recites typical equilibrium partial pressures for oxygen and carbon dioxide. For gases at ambient temperature and pressure, the partial pressures (in kPa) are approximately numerically equal to the molar, or volumetric, percentage concentrations. In aspects, the mass exchange apparatus may additionally be provided with flow headers and dividers in accord with conventional mass exchange apparatus and heat exchange apparatus design practice.

Figure 2:
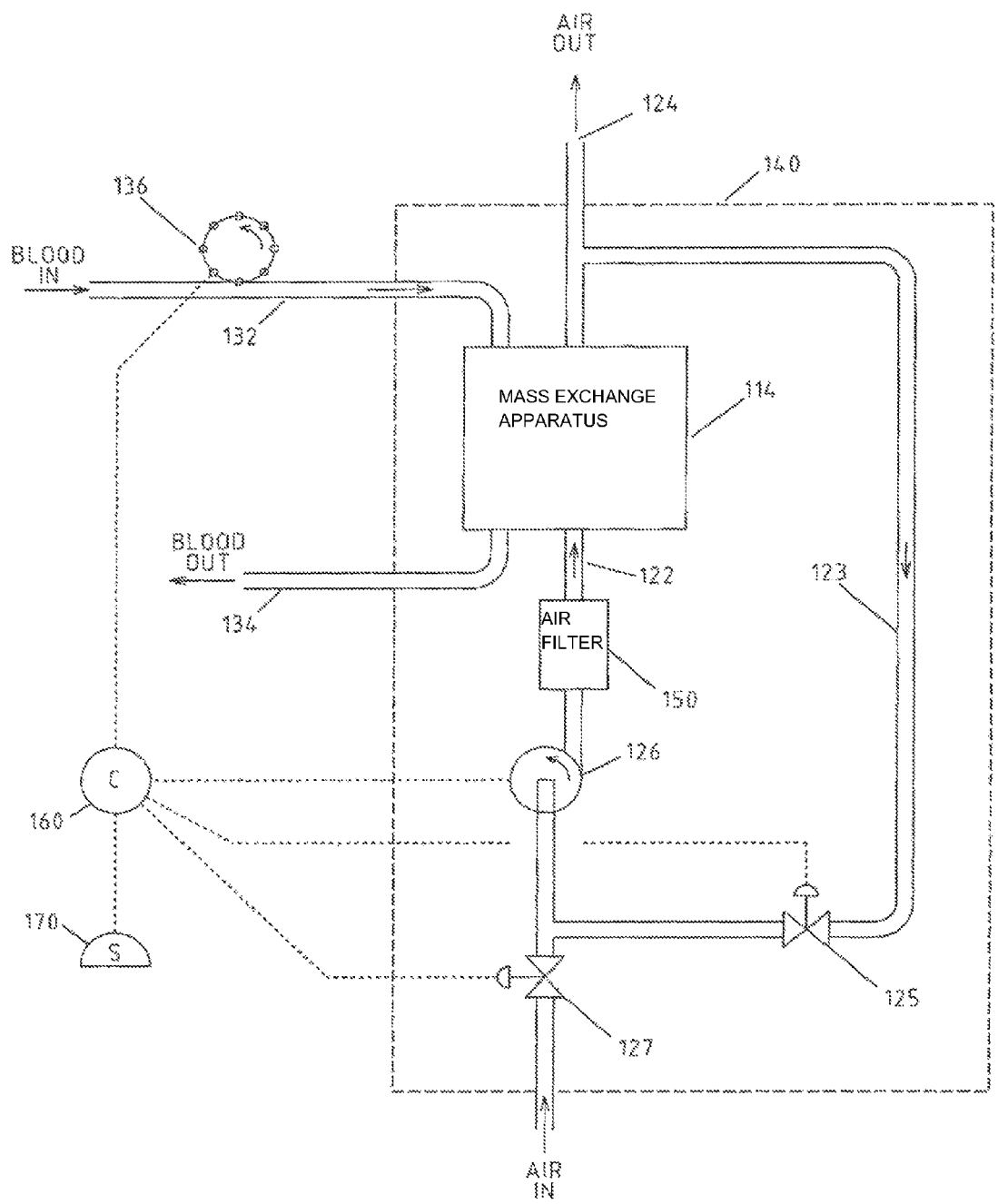
FIG. 2 shows a schematic representation of an external respiratory aid herein as suitable for connection to a patient.

FIG. 2 illustrates an external respiratory aid apparatus herein shown in cutaway view. The external respiratory aid 140 comprises an air/blood mass exchange apparatus 114 herein connected up to air and blood flow apparatus. Whilst in the embodiment shown in FIG. 2 there is a single mass transfer apparatus 114, variations are envisaged in which two mass exchange apparatus 114 are arranged in parallel fashion.

To create the air flow, air inlet 122 leads from pump 126 (e.g. in the form of a fan) to direct air in a first direction through the mass exchange apparatus 114 (e.g. having the detailed form of the mass exchange apparatus of FIG. 1), from which it exits at air outlet 124. In use, the air flow is controlled by suitable control of the air pump 126. It will also be seen that recycling channel 123 may be used to recycle air. Restrictor valves 125 and 127 are employed to control the amount of recycled air employed that is pumped back to the air inlet 122. In one variation herein, a pressure release valve (not shown) is inserted between the air pump 126 and mass exchange apparatus 114.

The patient's blood flows into the mass exchange apparatus 114 by means of blood inlet 132 and exits via blood outlet 134. It will be appreciated that the blood flow inlet 132 and outlet 134 are connected to the patient's blood supply. Blood flow is governed by the pumping action of blood flow pump 136. The pump is designed to minimize damage to the circulating blood flow. A number of pump designs are possible, and a peristaltic pump is illustrated. The respiratory aid apparatus 140 is also connected up to an air filter 150 that may also act as a humidifier. Optionally, the air can also be pre-heated with a simple heat exchange apparatus in contact with the body. As illustrated, the blood flows in a first direction through the apparatus 140 and the air flows in a second direction counter to the direction of blood flow.

The air flow pump 126; restrictor valves 125, 127; and blood flow pump 136 may be seen to communicate with controller 160, which in turn communicates with sensor 170. The sensor 170 is arranged to sense the respiratory demand of a patient (not shown) by sensing of the patient's pulse rate. The pulse rate input may be augmented by additional inputs; for example, the oxygen saturation of the venous blood entering the mass exchanger may be sensed. The controller 160 controls the pumping action of both pumps 126, 136 in response to signals received from the sensor 160, and hence acts to control the rate of blood/air mass exchange. The controller 160 also controls restrictor valves 125 and 127 and hence the air recycling action within the apparatus, which acts to control the levels of carbon dioxide and oxygen in the air flow in response to sensed patient respiratory demand.

Figure 3:
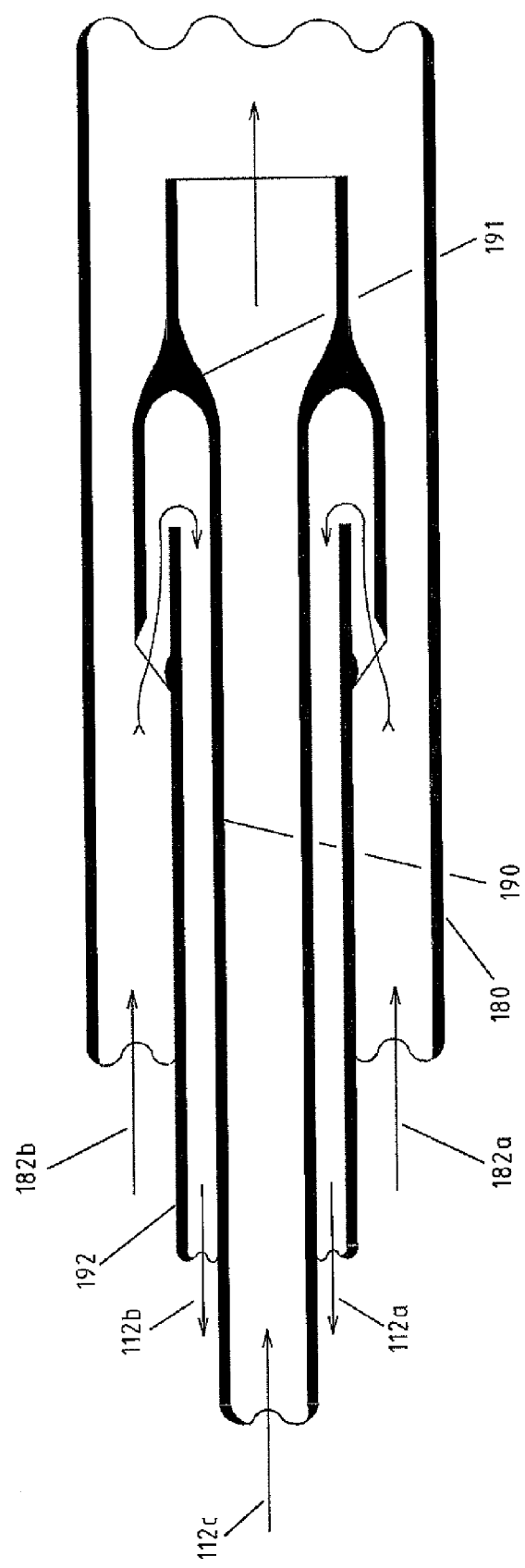
FIG. 3 shows a schematic representation of a possible extraction/return system for the external respiratory aid herein.

Desirably, the input tubing 132 to the blood pump 136 is arranged to provide blood extraction and return via a single entry point in a vein of a patient. An extraction head, which is suitable for installation by use of concentric input tubing 132, is illustrated in FIG. 3 herein. An alternative extraction head using adjacent tubing is illustrated in FIGS. 9a and 9b herein.

Referring now to FIG. 3, the vein 180 of a patient receives first 190 and second 192 concentric tubes. The tubing is arranged such that the blood flow 182a-b within the vein is counter to the blood flow 112a, 112b to the mass exchange apparatus, which flows in the outer concentric tube 192. In turn, the blood flow from the mass exchange apparatus 112c within the inner concentric tube 190 flows counter to the blood flow 112a, 112b to the mass exchange apparatus.

In the arrangement shown in FIG. 3, the extraction point is immediately upstream of the return point. The external surface of the extraction/return head is designed so that the device can be inserted into the vein 180 at a convenient point and then threaded to a suitable point, for example in the vena cava system. The design also allows withdrawal of the device without major surgery. In this way, the use of the external respiratory aid is easily reversible. A similar design, as illustrated at FIGS. 9a and 9b, applies for the case where the extraction and return channels are side-by-side, rather then concentric.

At the point of extraction, the outer tube (annulus) may have holes or a mesh through which the blood is extracted. The extracted blood 112a, 112b reverses direction to flow through the extraction tube. The returned blood 112c is arranged to flow in the same direction as the blood 182a, 182b in the vein from which it is extracted. By suitably tapering 191 the inner concentric tube 190 at the return point, the returned flow can mingle with the residual flow in the vein with both flows at approximately the same average velocity.

In alternative embodiments, and as shown at FIG. 9, the vein 680 of a patient receives input tubing comprising two tubes 690, 692 in side-by-side arrangement and received within a third tube 694 of circular cross-section. The tubing is arranged such that the blood flow 682a-b within the vein is counter to the blood flow 612a, 612b to the mass exchange apparatus, which flows in one tube 692. In turn, the blood flow from the mass exchange apparatus 612c within the other tube 690 flows counter to the blood flow 612a, 612b to the mass exchange apparatus. This arrangement provides the insertion of a single smooth round tube 694, with no crannies, that minimizes clotting on the outside. It avoids the complex point in which the inside tube has to be brought through the outside tube when the concentric tubes become parallel tubes. That is a point at which potentially blood clots may form.

Figure 4:
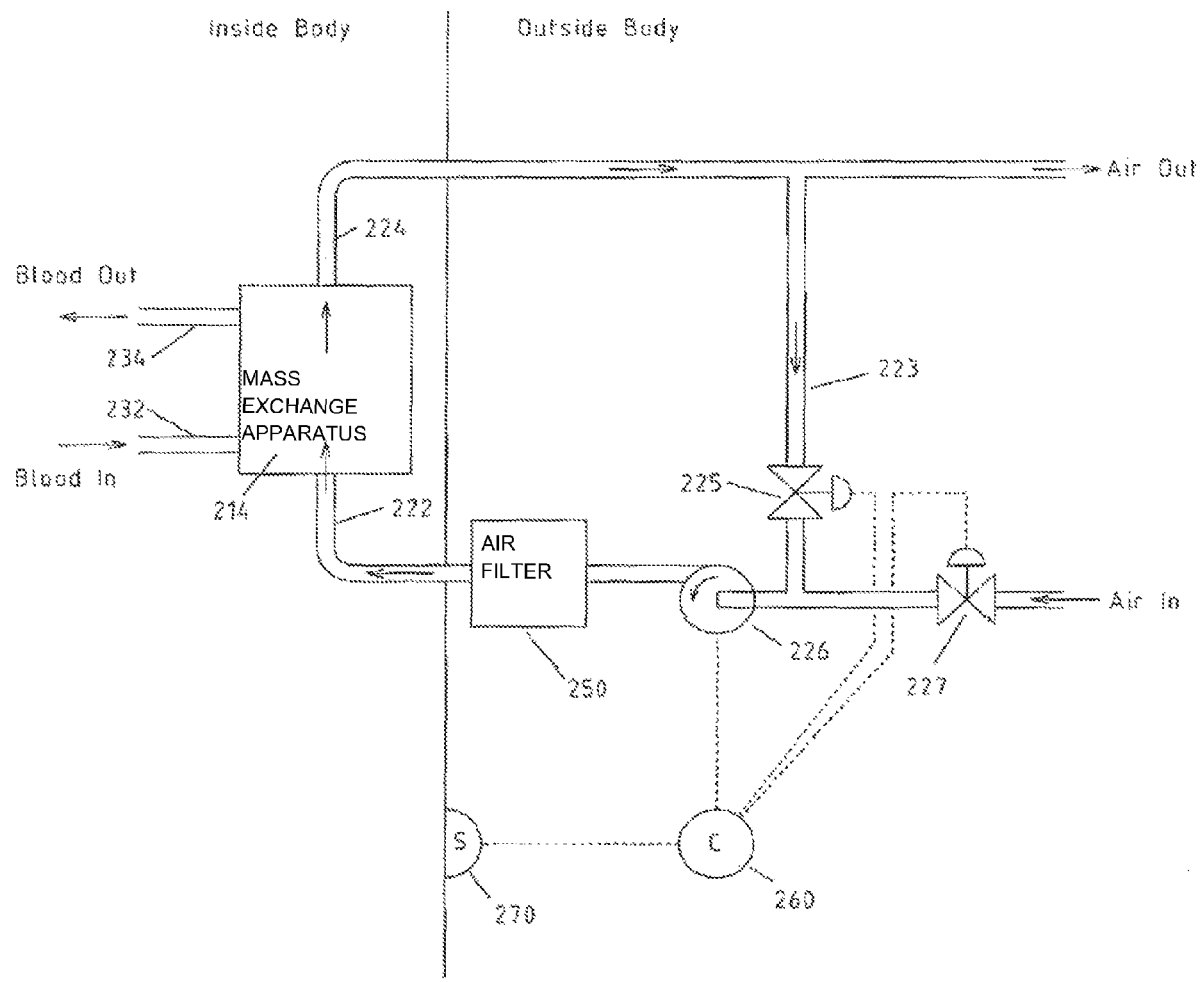
FIG. 4 illustrates a schematic representation of an intermediate respiratory aid apparatus herein.

FIG. 4 illustrates an intermediate respiratory aid apparatus herein shown in cutaway view. Part of the apparatus locates within the body of a patient and part locates outside of the body.

The intermediate respiratory aid comprises an air/blood mass exchange apparatus 214 herein (e.g. having the detailed form of that apparatus of FIG. 1) connected up to air flow apparatus. The mass exchange apparatus 214 is arranged to connect directly with a vein of a patient such that the blood flow is provided by the action of the patient's own heart. To create the air flow, air inlet 222 leads from pump 226 (e.g. in the form of a fan) to direct air in a first direction through the mass exchange apparatus 214 from which it exits at air outlet 224. In use, the air flow is controlled by suitable control of the air pump 226. Blood flows through the mass exchange apparatus 214 (in response to the action of the patient's heart) by means of blood inlet 232 and exits via blood outlet 234.

The air flow is delivered through a HEPA filter to clean the air before delivering it to the mass exchange apparatus 214. It will also be seen that recycling channel 223 is used to recycle air from the outlet 223. Restrictor valves 225 and 227 are employed to control the amount of recycled air employed that is pumped back to the air inlet 222. As for the external device, the air feed may also be humidified and pre-heated if required. In one variation herein, a pressure release valve (not shown) is inserted between the air pump 226 and mass exchange apparatus 214.

The air flow pump 226; restrictor valves 225, 227; and blood flow pump 236 may be seen to communicate with controller 260, which in turn communicates with sensor 270. The sensor 270 is arranged to sense the respiratory demand of a patient (not shown) by sensing of the patient's pulse rate. The pulse rate input may be augmented by additional inputs; for example, the oxygen saturation of the venous blood entering the mass exchanger may be sensed. The controller 260 controls the pumping action of both pumps 226, 236 in response to signals received from the sensor 260, and hence acts to control the rate of blood/air mass exchange. The controller 260 also controls restrictor valves 223 and 225 and hence the air recycling action within the apparatus, which acts to control the levels of carbon dioxide and oxygen in the air flow in response to sensed patient respiratory demand.

Figure 5:
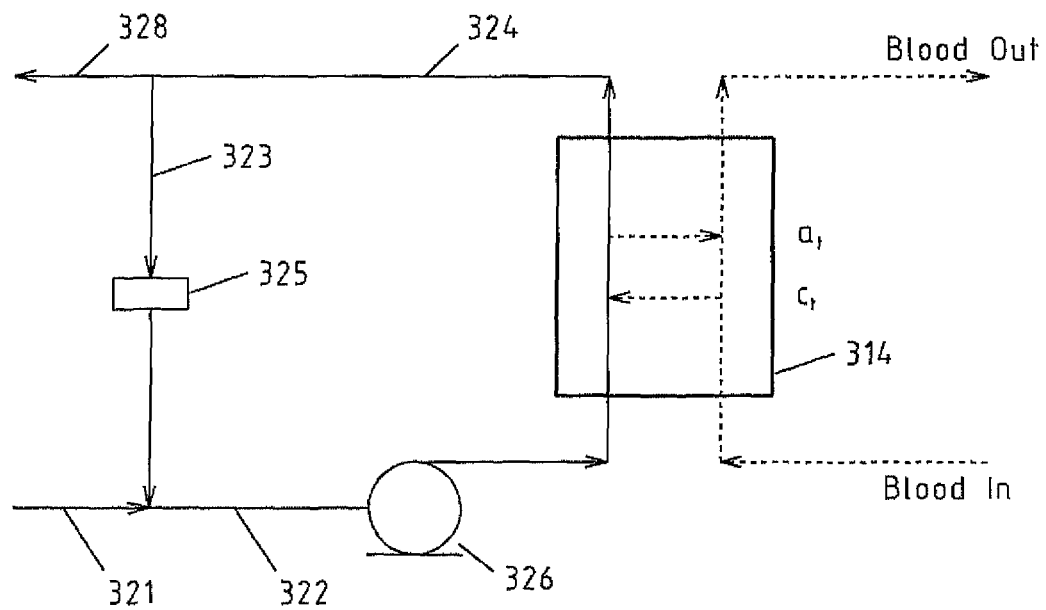
FIG. 5 illustrates a schematic representation of first control arrangement for use with a mass exchange apparatus herein, which employs an air feed and recycle.
Figure 6:
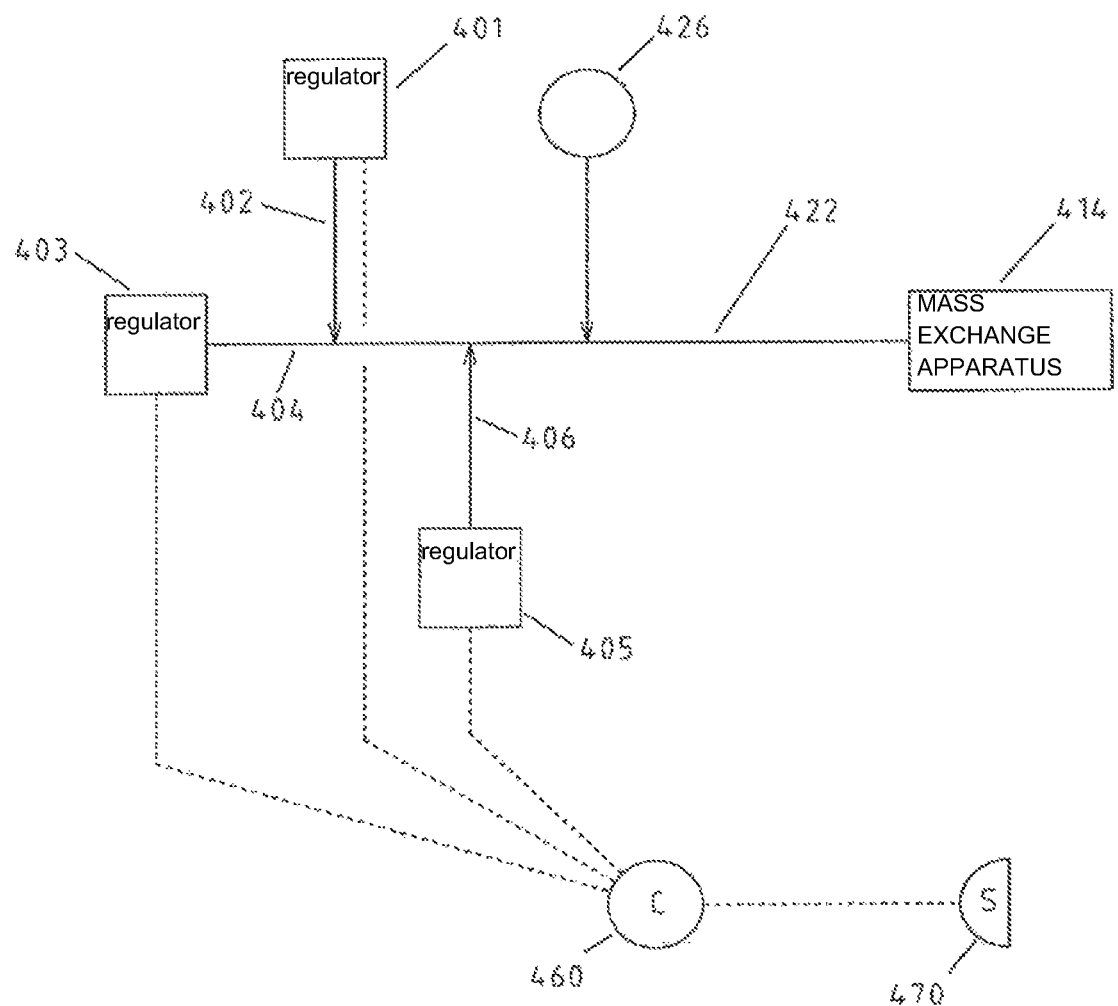
FIG. 6 illustrates a schematic representation of second control arrangement for use with a mass exchange apparatus herein, which employs multiple (pure) gas feeds.

The present invention requires separate control of carbon dioxide and oxygen levels in the air flow of the mass exchange apparatus. FIGS. 5 and 6 illustrate two different aspects of this control function, which may for example, be implemented using the basic apparatus of either FIG. 2 or 4. In both aspects, the flow rate of blood through the mass exchange apparatus 114; 214 is either taken as the whole flow in a vein or, using a controlled pump, adjusted to be a constant fraction of the total blood flow.

In the first aspect, natural air is employed. Natural air (filtered and/or humidified) is mixed with a recycle 123; 223 from the mass exchange apparatus 114, 214 and the mixed stream fed to the mass exchange apparatus. The output from the mass exchange apparatus 114; 214 is divided, part is recycled and part is exhausted to atmosphere. There is a pump (or fan) in the recycle loop 123, 223 and one or more valves 125, 127; 225, 227 to control the proportion of gas recycled. Both the oxygen and carbon dioxide concentrations can be controlled by suitably adjusting the pumping rate and the recycle proportion (which adjusts the net feed and exhaust rates).

The patient respiratory demand is sensed by sensor 170; 270 and the oxygen and carbon dioxide concentrations are adjusted responsive thereto by the control action of controller 160; 260 to provide the required mass transfer rates and concentrations. As a specific example, pulse rate can be employed to sense respiratory demand. A high pulse rate implies a high blood circulation rate which requires high oxygen and carbon dioxide mass transfer rates. Conversely, a low pulse rate implies a low circulation rate and a low patient respiratory demand. In addition to (or instead of) pulse rate, other non-intrusive measures of respiratory demand can be employed.

For example, we could measure strength of the pulse, or blood oxygen saturation. Other methods, essentially based on measuring noise, can also be employed to estimate circulation rate. There is a strong preference for non-intrusive sensing of patient respiratory demand. We wish to minimize risk of blood clotting and minimize use of sensitive instruments that may be damaged in normal use by a mobile conscious patient. Any sensor 170; 270 permanently placed in the blood stream risks stimulating clotting, or losing sensitivity through fouling. Any device that permanently requires a small bleed of blood presents similar problems and provides an additional point for ingress of infection.

In use of the mass exchange apparatus, the concentration levels are initially adjusted so that, at rest, the patient has a comfortable heart rate.

In FIG. 5, there are five components to the overall air flow stream:
Stream 1 is the air flow input 321 from the atmosphere
Stream 2 is the air flow input 322 to the mass exchanger 314
Stream 3 is air flow output 324 from the mass exchanger 314
Stream 4 is the air flow recycle stream 323
Stream 5 is the stream of exhaust gas 328 discharged to atmosphere.
$a_t$ Mass transfer rate of oxygen from gas phase, through membrane, to blood
$c_t$ Mass transfer rate of carbon dioxide from blood, through membrane, to gas phase
We employ the following symbols:
$a_i$ Flow rate of oxygen in stream "i"
$n_i$ Flow rate of nitrogen in stream "i"
$c_i$ Flow rate of carbon dioxide in stream "i"
wherein "i" takes the value 1, 2, 3, 4 or 5.

The pump/fan 326 may alternatively be placed in the exit stream from the mass exchange apparatus 314. The benefit of placement in the exit stream is that risk of over-pressurization in the mass exchange apparatus is eliminated. A valve restrictor (not illustrated) may be placed in the feed stream 321 (or alternatively, in the exhaust stream 328) to stimulate recycle flow. If in the feed stream 321, it produces a low pressure in air flow input 322 at the junction with the air flow recycle stream 323. This low pressure creates a pressure difference across the valve restrictor 325, which enables the recycle flow rate to be controlled. If alternatively, the valve restrictor is in the exhaust stream 328, it produces a high pressure at the junction of air flow output steam 324 and the air flow recycle stream 323. This high pressure also creates a pressure difference across the valve restrictor, which allows the recycle rate to be adjusted. The flow area of the valve restrictor 325 may also be adjustable so that total pressure in the system can be adjusted to just below blood pressure (to prevent risk of gas leaking through the membrane and causing bubbles in the blood).

Note that FIG. 5 does not illustrate the mechanism by which the blood is pumped through the mass exchange apparatus 314. Suitable methods have previously been described by reference to FIGS. 2 and 4. Also note that FIG. 5 illustrates only co-current flow through the mass exchange apparatus 314. The present invention allows also for counter-current or mixed flow.

For every blood flow rate, we have target inlet and outlet blood gas partial pressures. In order to provide the desired transfer rates, we require appropriate mean driving forces for both oxygen and carbon dioxide. These mean driving forces are achieved by setting inlet and outlet concentrations of oxygen and carbon dioxide.

Applying material balance, we obtain $$n_2 = n_1/(1-f)$$

$$n_3 = n_1/(1-f)$$

$$a_2 = (a_1 - fa_t)/(1-f)$$

$$a_3 = (a_1 - a_t)/(1-f)$$

$$c_2 = fc_t/(1-f)$$

$$c_3 = c_t/(1-f)$$

The relevant mole fractions are:

| | |
|---|---|
| Inlet mole fraction of oxygen | $x_{a2} = (a_1 - fa_t)/(a_1 + n_1 - fa_t + fc_t)$ |
| Outlet mole fraction of oxygen | $x_{a3} = (a_1 - a_t)/(a_1 + n_1 - a_t + c_t)$ |
| Inlet mole fraction of carbon dioxide | $x_{c2} = fc_t/(a_1 + n_1 - fa_t + fc_t)$ |
| Outlet mole fraction of carbon dioxide | $x_{c3} = c_t/(a_1 + n_1 - a_t + c_t)$ |

In the above equations, f is the fraction of Stream 3 that is recycled. With 100% recycle, the inlet and outlet compositions are equal. The outlet compositions are independent of recycle fraction. With smaller recycle fractions, the inlet concentration of carbon dioxide is reduced and the inlet concentration of oxygen is increased. Note that the total feed rate is $(a_1 + n_1)$. The oxygen feed rate is a constant fraction of the total feed rate. The area must be sufficient to support the maximum mass-transfer rate without incurring excess pressure drop. With this proviso, the above equations can be solved for any mean driving-force formula, to give desired values of total feed rate and of recycle fraction.

The targeted mean driving forces depend on the particular mode of operation of the mass exchange apparatus 314 herein.

We first consider the case when the mass exchange apparatus 314 is deployed to provide the majority of the mass transfer. For example, it takes the majority of the blood flow and the lungs are very deficient. In these circumstances, the mass transfer rate and concentrations must closely match those of the natural lung. We then find, by inserting typical values that the mass exchange apparatus 314 must operate in co-current mode.

However, where the mass exchange apparatus 314 is deployed to take only a fraction of the flow, it may improve performance to reduce the outlet blood carbon dioxide concentration. There may then be the option to apply the mass exchange apparatus 314 either in co-current or counter-current mode. The blood with reduced carbon dioxide can be mixed with blood having excessive carbon dioxide that bypasses the mass exchange apparatus 314. The resulting mixture may have close to the natural carbon dioxide concentration. The benefit of counter-current flow is that a smaller mass exchange apparatus 314 may be needed. The control algorithm is readily adjusted to account for such situations with the same basic processes (such as illustrated at FIG. 5) described herein.

Note the contrast between this approach and that described in U.S. Pat. No. 3,927,981. Herein, recycle is used to deliberately concentrate carbon dioxide in the recycle loop. In this way, we avoid excessively depleting blood carbon dioxide levels. In contrast, the approach described by U.S. Pat. No. 3,927,981 removes all carbon dioxide from their recycle stream. We use air (or a feed containing a high proportion of inert gas). In this way, we can control the mass transfer rate by adjusting oxygen and carbon dioxide concentrations. In contrast, the approach described by U.S. Pat. No. 3,927,981 favours a pure oxygen feed, which results in an intrinsically unstable system.

In the second aspect illustrated at FIG. 6, three gas streams are employed. Stream "a" is a pure oxygen stream 402. Stream "n" is an inert gas stream 404, for example pure nitrogen. Stream "c" is a pure carbon dioxide stream 406. A flow regulator 401, 403, 405 is employed for each respective stream 402, 404, 406 before they are mixed. The streams 402, 404, 406 combine to form the air flow inlet 422 to the mass exchange apparatus 414. Other details of the mass exchange apparatus 414 are not shown, but they may correspond to any of those previously described.

Also shown is a pressure relief valve 426 set to open if the total pressure is higher than can be safely employed in the mass exchange apparatus 414.

Each of the flow regulators 401, 403, 405 may be seen to communicate with controller 460, which in turn communicates with sensor 470. The sensor 470 is arranged to sense the respiratory demand of a patient (not shown) by sensing of the patient's pulse rate. The pulse rate input may be augmented by additional inputs; for example, the oxygen saturation of the venous blood entering the mass exchanger may be sensed. The controller 460 controls the flow regulating action of each of the flow regulators 401, 403, 405 in response to signals received from the sensor 460, and hence acts to vary the levels of carbon dioxide, oxygen and inert gas of the inlet air flow 422, and thus, the rate of blood/air mass exchange.

Thus, FIG. 6 illustrates a mechanism for mixing three gases including the following features:
1) The realization that all three gases (oxygen, carbon dioxide and inert gas) must be present
2) The controller 460 that adjusts the concentrations of oxygen and carbon dioxide so that mass transfer rates respond to respiratory demand
3) The means of estimating respiratory demand. For example, estimated by monitoring patient pulse rate as sensed by the sensor 470

For long-term use on patients who may not be closely monitored, the second approach illustrated by FIG. 6 may be riskier than the first approach illustrated at FIG. 5. Thus, if any one of the controlled flow regulators 402, 402, 406 fails, a gas mixture could pass through the mass exchange apparatus 414 that causes death within seconds. The risk is present both for fail-open and for fail-closed conditions.

The risk can be reduced by using three mixed gas supplies instead of three pure gas supplies. For example, "stream n" 403 could be a nitrogen/oxygen/carbon dioxide mixture with sufficient oxygen to support life at rest. The carbon dioxide concentration would be high enough to guard against respiratory shut-down. Similarly, the other feeds would also have concentrations that would, if used on their own, support life.

A simpler variant to that shown at FIG. 6 has just two feed streams, one suitable for mass transfer at rest and the other for mass transfer under maximum exertion. The controller 460 then only manipulates two flow regulators to give a composition appropriate for any level of respiratory demand between rest and maximum exertion. (The actual feed-stream concentrations would depend on the mass exchange apparatus area and on how the mass exchange apparatus 414 was deployed). This approach would greatly reduce the risks of equipment failure. Compared with using an air feed, there is still the risk that an incorrect cylinder could be fitted. Such risks can be further reduced by including gas analysers for oxygen and carbon dioxide. Any system using bottled gas supplies will be non-portable. Hence, the additional weight of analysers would not be significant. The mixing (as illustrated in FIG. 6) is done remote from the patient (with remote monitoring of pulse rate) and the mixed gases supplied through a sufficiently long feed tube to allow mobile patients to exercise. In all cases, the exhaust from the mass exchange apparatus 414 is discharged to atmosphere (possibly after passage through a heat exchanger).

The present invention encompasses intermediate systems between the two aspects described above. For example, there could be an air feed 322 with recycle 323 with a second feed with an enhanced oxygen concentration. Use of an enhanced oxygen concentration can reduce the mass exchange area. However, it is appreciated that the size and mass of any bottled gas feed exceeds the size and mass of a larger mass exchange apparatus using natural air.

Details of Control

The Applicant has recognized that control is of particular importance for two reasons. The first reason arises because a mass exchange apparatus for use in blood oxygenation is typically a continuous flow apparatus of fixed area. The second reason arises because the mass transfer coefficient for carbon dioxide in a mass exchange apparatus is typically more than an order of magnitude greater than that for oxygen. In contrast, a natural lung pumps at a rate depending on respiratory demand. Breathing is both faster and deeper during periods of high demand. Furthermore, the mass transfer coefficient for carbon dioxide in natural lungs is only about a factor of two greater than that for oxygen.

With natural, well-functioning lungs, increased respiratory demand is met by increased heart rate, and deeper and faster breathing. In this way, more blood circulates around the body, more oxygen is supplied to the blood through the lungs, and more carbon dioxide is removed from the blood by the lungs. With defective lungs, the heart rate will still increase in response to increased respiratory demand. However, the defective lungs are incapable of supplying more oxygen. Augmenting defective lungs with a mass exchange apparatus may enable the respiratory demand to be met under resting conditions. However, in response to any increase in respiratory demand, the mass exchange apparatus will not respond with increased oxygenation unless specific control action is taken. We consider, in turn, the three control actions needed:
1) Control of blood flow rate through the mass exchange apparatus
2) Control of oxygen mass transfer rate and blood oxygen concentration
3) Control of carbon dioxide mass transfer rate and blood carbon dioxide concentration.

1. Control of Blood Flow Rate Through the Mass Exchange Apparatus

We consider first the simple case in which the blood oxygen and carbon dioxide concentrations remain constant in response to varying respiratory demand. In this case, with normal lungs, the quantity of oxygen transported from the lungs is directly proportional to the blood flow rate. Similarly, the quantity of carbon dioxide exhausted from the lungs is directly proportional to blood flow rate. We require that, when blood flow rate through the body doubles, the mass transfer rates of oxygen and carbon dioxide through the mass exchange apparatus should also double. Under normal conditions, arterial blood leaving the lungs will be nearly saturated with oxygen. Similar saturation levels must be achieved in blood leaving a mass exchange apparatus. Thus, oxygen concentration leaving the mass exchange apparatus is approximately constant. In order to double the quantity of oxygen transported from the mass exchange apparatus, the flow rate of blood through the mass exchange apparatus must double. In general, the flow rate of blood through the mass exchange apparatus must be proportional to the blood flow rate through the heart. Where the whole flow of blood from a vein is passed through the mass exchange apparatus, we automatically ensure that that the flow rate through the mass exchange apparatus is proportional to the circulation rate. At low to moderate exertion, the required control action can be achieved by setting the flow rate through the mass exchange apparatus proportional to heart rate. This proportionality may suffice for patients not expected to undertake strenuous activity. For more vigorous exertion, a correction must be applied related to the strength of the heart beat. There are additional benefits in taking a constant fraction of the blood flow rate in a vein. Specifically, we eliminate any risk that excessive blood extraction creates a locally reversed flow in the vein and that excessive shear rates or stagnant zones are created. To maintain concentrations at the same level as blood flow-rate changes, the mass transfer rates must also be proportional to blood flow rate.

We have shown the benefits of maintaining mass transfer rates proportional to blood flow rate. We now show the dangers of not maintaining a proportional, or more than proportional, mass transfer rate. Consider that mass transfer rates remain constant as blood flow-rate changes. Consider two cases, the first in which the blood carbon dioxide level is below the biological set point, the second in which it is above the set point. In the first case, the body will sense low carbon dioxide (and imply high oxygen). The in-built natural control mechanism will slow the respiration rate. Thus, it will slow the heart beat and slow breathing. (With defective lungs, slowing breathing will have little or no effect). If the lungs were working normally, the net effect would be a decrease in mass transfer rates so that the blood carbon dioxide would increase and blood oxygen decrease. The natural control mechanisms continue to slow respiration until the carbon dioxide concentration reaches the biological set point. At that stage, respiration settles at its new lower level. If our mass exchange apparatus continued to deliver constant mass-transfer rates, the same flow of oxygen would go into a smaller blood flow, thus increasing oxygen concentration. Similarly, the same amount of carbon dioxide would be removed from a smaller blood flow, thus decreasing carbon dioxide concentration. The natural control action would be confused. It expected carbon dioxide concentration to increase, whereas it decreased. It would slow the respiration rate even further. With no increase in carbon dioxide concentration, it would slow the respiration to a stop, when the patient would die. In the second case, the body will sense high carbon dioxide. The resulting behaviour is the inverse of the low carbon dioxide case. The body keeps increasing heart rate. For every increase, carbon dioxide concentrations are even higher.

The biological set point is unknown. Hence, the situation will always arise in which the actual blood concentration is either above or below the set point. Thus, a control system, which delivers constant mass-transfer rates, is intrinsically unstable. It either closes down the respiratory system or increases heart rate until it is dangerously high. A system that delivers mass transfer rates proportional to respiratory demand is more stable. Consider the case in which carbon dioxide concentration is less than the set point, and assume that, at rest, there is a constant residual metabolic rate. Then the metabolic processes consume a constant residual oxygen demand and deliver a constant flow of carbon dioxide into the blood. As the blood flow rate decreases, this constant production rate gives rise to an increasing blood carbon dioxide concentration. Thus, eventually the natural control mechanism will reduce the blood flow until the set point is reached. Similarly, if the initial blood carbon dioxide concentration is too high, the oxygenated blood flow rate will increase until the carbon dioxide concentration falls to the set point. It follows that a control system that delivers mass transfer rates proportional to respiratory demand is intrinsically more stable. Control stability may be improved by delivering mass transfer rates that vary more than proportionately with blood flow rate. The set point is then reached with a smaller excursion of heart rate from its value for light exercise. In the following sections, we consider first the steps necessary to deliver mass transfer rates proportional to respiratory demand. These steps can be extended to give a non-linear response that may further improve stability.

At rest, and under light exertion, blood circulation rate is proportional to pulse rate. At the same time, blood gas concentrations change little. Thus, respiration rate is also proportional to pulse rate. At higher respiration rates (for example, in athletic activities), the tissues take more oxygen from the blood. Thus, the venous blood returning to the lungs has lower oxygen concentration and higher carbon dioxide concentration. For patients expected to experience such high respiration rates, monitoring of the blood oxygen saturation is also required. The respiratory demand is then proportional to the product of the blood circulation rate and the difference between arterial and venous blood oxygen-saturation levels. Where the aim is to achieve high blood oxygen-saturations out of the mass exchange apparatus, it is only necessary to sense the venous blood oxygen saturation into the mass exchange apparatus.

2. Oxygen Mass Transfer

The relevant mass transfer equation is:

$$m = AU\Delta c \qquad (1)$$

In equation (1)

m is mass transfer rate, for example moles per second

A is the mass exchange apparatus interfacial area

U is the mass transfer coefficient $\Delta c$ is the driving force for mass transfer Consider a case in which the oxygen demand from metabolic processes doubles. In order to maintain the same oxygen concentration in the blood, the mass transfer rate must double. For a typical mass exchange apparatus (for example, of the membrane type), the interfacial area is fixed by geometry. The apparatus is rigid and cannot expand and contract to change its area. Within the very small blood and air flow channels (typically fractions of a millimeter) flows remain laminar. Hence, the mass transfer coefficient only varies slightly. Thus, in order to increase the mass transfer rate, the concentration difference must increase. For fixed blood oxygen concentrations, the gas-phase concentration of oxygen must increase.

Table 1 gives typical partial pressures for a healthy person. We will concentrate just on the blood phase equilibrium partial pressures. If the mass exchange apparatus is to reproduce the performance of the human lung, it must have the same input and output partial pressures. The mean driving force to use in equation (1) depends on the flow pattern and the relationship between concentration in blood and equilibrium partial pressure. (See, for example, Coulson J M and Richardson J F, Chemical Engineering, Volume 1 (Fluid Flow, Heat Transfer and Mass Transfer), Butterworth Heinmann, Oxford, 2000). Such values are needed for detailed design. However, we can illustrate the problem by taking a mean oxygen partial pressure over the blood. We take a value of 9 kPa, which is between the venous value of 5.3 and the arterial value of 12.3. Using air as the gas phase, the maximum mean air-side oxygen partial pressure is 21 kPa. That gives a mean driving force of around 12 kPa. To leave scope to respond to high respiratory demand, the normal mean driving force should be less than the maximum. If we are to give the patient a 2:1 respiratory range, it should be half the maximum. In that case, for normal operation, we should have a mean driving force of no more than 6 kPa. The corresponding mean gas partial pressure is 15 kPa (which corresponds to 15% oxygen). For wider dynamic ranges, lower normal operating partial pressures are required. Thus, we would operate with a considerably lower mean partial pressure than is the case for normal lungs. (For normal lungs the gas-side partial pressure lies between 21 kPa on the in breath and 16 kPa on the out breath). If a synthetic gas mixture is employed, it is possible to use pure oxygen to generate the maximum mean driving force. The resulting driving force is (100−9)=91 kPa. For normal operation, the driving force should be a fraction of this maximum pressure difference. For example, for a 2:1 dynamic range, it should be about half the maximum. Thus, for normal conditions, the mean oxygen partial pressure should be about 54 kPa. For example, the oxygen may enter with a partial pressure of 56 kPa (gas mixture of 56 mole percent oxygen) and leave with a partial pressure of 52 kPa (mixture having 52 mole percent oxygen).

This simple illustration shows the importance of employing a mixed gas feed, not pure oxygen. When pure oxygen is employed, anything which increases metabolic rate above the resting rate (exercise, excitement or worry) risks leaving oxygenation rates uncontrollable.

3. Carbon Dioxide Mass Transfer

Equation (1) applies equally to Carbon Dioxide mass transfer. The mass transfer coefficient for carbon dioxide is so high that carbon dioxide will leave the blood until there is a very small driving force. The control problem is then not to transfer sufficient carbon dioxide, but to control the blood carbon dioxide concentration by maintaining a sufficient gas-side partial pressure. Consequently, there is a problem with both pure air and pure oxygen feeds. In both cases, the concentration of carbon dioxide in the feed is zero, or close to zero. We show below that the concentration (partial pressure) of carbon dioxide is likely also to be low at the outlet of the mass exchange apparatus. Hence, there is limited scope for controlling the blood carbon dioxide concentration. For co-current flow, the equilibrium partial pressure will approximately equal the outlet gas concentration. It will be proportional to the metabolic rate divided by the gas flow rate. Thus, we need to control the gas-phase inlet carbon dioxide concentration in order to control the blood carbon dioxide concentration. The very high carbon dioxide mass transfer coefficients provide a particular problem that needs to be overcome in any practical design. Relative mass transfer coefficients are estimated in Tables 2 and 3.

TABLE 1

Oxygen and Carbon Dioxide Partial Pressures.

| Stream | Oxygen Partial Pressure, kPa | $CO_2$ Partial Pressure, kPa |
|---|---|---|
| Atmospheric Air Input | 21.0 | 0.0 |
| Venous Blood Input | 5.3 | 6.3 |
| Exhaled Air Output | 16.0 | 4.0 |

TABLE 1-continued

Oxygen and Carbon Dioxide Partial Pressures.

| Stream | Oxygen Partial Pressure, kPa | $CO_2$ Partial Pressure, kPa |
|---|---|---|
| Arterial Blood Output | 12.3 | 5.3 |
| Alveolar Air | 13.3 | 5.3 |

The values in Table 1 are indicative average values. In practice, they differ from person to person, and are difficult to measure accurately, as illustrated by the figures in Table 1a. (Nemery B, Nullens W, Veriter C, Brasseur L and Frans A, Effects of Gas Density on Pulmonary Gas Exchange of Normal Man at Rest and During Exercise, Pflügers Arch, pp 57-61, 1983). The values in Table 1a were obtained for breathing air, and averaged from measurements on six healthy males at rest.

TABLE 1a

Oxygen and Carbon Dioxide partial Pressures breathing air.

| Stream | $O_2$ PP, kPa | Standard Deviation. | $CO_2$ PP, kPa | Standard Deviation. |
|---|---|---|---|---|
| Arterial Blood | 12.7 | 1.3 | 5.01 | 0.72 |
| Alveolar Air | 14.2 | 1.4 | 4.96 | 0.84 |
| Difference | 1.5 | 0.5 | 0.06 | 0.16 |

The figures in Table 1 are all within one standard deviation of the figures in Table 1a. The differences (driving forces for mass transfer) must all be positive. Hence, the statistics for carbon dioxide driving force are inappropriate. They merely indicate that the driving force is extremely low. The same reference gives the ratio of carbon dioxide mass transfer rate to oxygen mass transfer rate as 0.90, with a standard deviation of 0.14. This ratio is in molar (or volumetric) units.

We do not need accurate figures to illustrate the control problem when we switch to membrane mass-transfer devices. The relevant changes are order-of-magnitude effects. Accordingly, we will use the figures from Table 1 apart from the estimated driving force between alveolar air and arterial blood. For this case, we will consider driving forces between 0.0 and 0.06 (as given in Table 1a).

Similarly, in considering the overall driving forces in the human lung, we do not need an accurate model of the steps in the mass transfer process. In an accurate model of breathing within the lungs, the alveolar air is separated from the inlet air by a volume in which mixing occurs (often modelled as a dead volume). Thus, the alveolar air composition varies little during the breathing cycle. This dead volume and the bronchial passageways can be lumped into an overall mass transfer resistance between the air at the mouth (nose) and the carbon dioxide in the blood. Similarly, the resistance can be averaged over the breathing cycle.

With these simple lumped resistances, equation (1) gives, for the overall breathing cycle in the natural lungs:

$$U_{CO2}/U_{O2}=(m_{CO2}/m_{O2})(\Delta c_{O2}/\Delta c_{CO2}) \qquad (2)$$

Notice that the area from equation (1) cancels because it is the same for both gases. Further note that published data gives $(m_{CO2}/m_{O2})=0.9$. Hence, equation (2) further simplifies to:

$$U_{CO2}/U_{O2}=0.9(\Delta c_{O2}/\Delta c_{CO2}) \qquad (3)$$

The relevant mean driving forces depend on whether the blood and air flows are considered to be co-current or counter-current. For a cyclic breathing process, a mean between co-current and counter-current applies. Hence, we will scope the range of values by considering the two extremes. For both flow patterns, we take the relevant logarithmic mean driving forces (see Coulson and Richardson). The logarithmic mean between values "$c_1$" and "$c_2$" is $$c_{mean} = (c_1 - c_2)/\ln(c_1/c_2)$$

Table 2 gives the steps in the calculation of the relative mass-transfer coefficients for lungs.

TABLE 2

Calculation of relative mass transfer coefficients in human lungs.

|  |  | $\Delta c_1$ | $\Delta c_2$ | $\Delta c_{mean}$ | $U_{CO2}/U_{O2}$ |
|---|---|---|---|---|---|
| Co-current | $CO_2$ | 6.3 − 0.0 = 6.3 | 5.3 − 4.0 = 1.3 | 3.17 |  |
|  | $O_2$ | 21 − 5.3 = 15.7 | 16 − 12.3 = 3.7 | 8.31 |  |
|  |  |  |  |  | 2.62 |
| Counter-current | $CO_2$ | 5.3 − 0.0 = 5.3 | 6.3 − 4.0 = 2.3 | 3.59 |  |
|  | $O_2$ | 21 − 12.3 = 8.7 | 16 − 5.3 = 10.7 | 9.67 |  |
|  |  |  |  |  | 2.69 |

Thus, the ratio of mass transfer coefficients is about 2.5. The significance of the ratio is that, for the same driving force, the rate of mass transfer of carbon dioxide is 2.5 times greater than that of oxygen. Alternatively, for the same mass transfer rate, the driving force for carbon dioxide can be 2.5 times less.

pressure of carbon dioxide in the gas phase, but it can be estimated by material balance and the estimated value is given in Table 3. They did not report the equilibrium partial pressures for blood oxygen at inlet or outlet. However, the gas partial pressures are so high that an approximate estimate of the blood values is sufficient. The values are taken from Table 1. Their oxygen and carbon dioxide transfer rates are reported as 45 and 70 ml/min respectively. The ratio of molar transfer rates is thus 70/45=1.556, instead of the expected value of 0.9 used in table 2. The flow in the Viannay and Sousse patent is co-current.

TABLE 3

Calculation of relative mass transfer coefficients for membrane mass exchange.

|  |  | $\Delta c_1$ | $\Delta c_2$ | $\Delta c_{mean}$ | $m_{CO2}/m_{O2}$ | $U_{CO2}/U_{O2}$ |
|---|---|---|---|---|---|---|
| Table 1 | $CO_2$ | 6.3 − 5.6 = 1.0 | <0.06 | <0.33 |  |  |
|  | $O_2$ | 13.3 − 12.3 = 1.0 | 13.3 − 5.3 = 8.0 | 3.366 |  |  |
|  |  |  |  |  | 0.9 | >9 |
| Viannay et al. | $CO_2$ | 6.66 − 0.0 = 6.66 | 5.33 − 0.5 = 4.83 | 5.696 |  |  |
|  | $O_2$ | 101.3 − 5.6 = 95.7 | 100.8 − 11.9 = 88.9 | 92.26 |  |  |
|  |  |  |  |  | 1.5556 | 25.2 |

Table 3 gives the corresponding calculations for membrane mass exchange apparatus with negligible mass transfer resistance in the membrane. A membrane mass exchange apparatus eliminates the gas-side mass-transfer resistance. Thus, there is no dead volume and no length of bronchi for the gases to diffuse through. However, the blood-side mass-transfer resistance remains similar. For oxygen, the resistance results from diffusion of the oxygen through the liquid phase, diffusion into the red corpuscles and the relatively slow reaction of dissolved oxygen with haemoglobin. For carbon dioxide, the resistance results from diffusion through the liquid phase and the reaction of dissolved carbon dioxide to form primarily bicarbonate ions. The average diffusion distance is less for carbon dioxide because bicarbonate ions can form throughout the bulk of the liquid. The equilibration to bicarbonate ions is made rapid by the presence of the catalyst, carbonic anhydrase, in the blood. We give two independent estimates of the relative mass-transfer coefficients. The first comes from Table 1 and Table 1a in which we consider only the blood-side transfer by calculating the transfer between the alveolar air and the blood. The second comes from membrane-oxygenator mass-transfer measurements reported by Viannay and Sousse in U.S. Pat. No. 3,927,981. The calculation is summarized in Table 3. Note that Viannay and Sousse reported pressures in mm Hg (torr). These pressures have been converted to kPa. Viannay and Sousse used a pure oxygen feed at approximately STP. They did not report the outlet partial The results from Viannay et al are consistent with the results expected from Table 1. In both cases, the uncertainty in the calculations is large. Nevertheless, comparing Table 2 and Table 3, we see that the relative mass transfer coefficient for carbon dioxide is roughly a factor of 10 greater in a mass exchange apparatus than a human lung.

We now address the practical problem posed by this very large mass transfer coefficient. The significance of the high value noted is that, for equal oxygen and carbon dioxide molar transfer rates, the driving force for carbon dioxide is less than 5% of that for oxygen. Indeed, as for mass transfer from alveolar air to arterial blood, in Tables 1 and 1a, the driving force may be indistinguishable from zero. Consider transfer with natural air, and consider the same mean air flow rate as in Table 1. For counter-current flow, the arterial carbon dioxide partial pressure equals that of the inlet air (i.e. nearly zero). For co-current flow, the arterial carbon dioxide partial pressure would equal that in the exhaled air, namely 4 kPa. In both cases, the carbon dioxide concentration would be much lower than the level expected by the body's natural control mechanism. There is risk of respiratory shut down. If the mass transfer coefficients were in the same proportion in lungs and mass exchange apparatus, the design problem would be relatively straightforward. Thus, using natural air, a driving force that gave adequate blood oxygen concentrations would also give adequate blood carbon-dioxide concentrations. However, with relatively much higher carbon dioxide mass transfer coefficients, it is necessary to increase the inlet gas carbon dioxide concentration in order to achieve satisfactory blood carbon-dioxide levels. Furthermore, blood carbon-dioxide level will not automatically respond appropriately to changes in oxygen mass-transfer rates. The present invention provides independent means of controlling blood oxygen and carbon dioxide levels. In this way, a suitable controller can mimic the natural relationship between blood oxygen and carbon dioxide levels. By mimicking the natural relationship, the natural respiratory control mechanism can respond to changing metabolic rates in an effective and stable manner.

Mixed Flow Mass Exchange Apparatus

In an alternative aspect herein, there is described an improved mixed-flow mass exchange apparatus with particular application in blood oxygenation. This aspect refines the design of a mass exchange apparatus as described in Applicant's earlier-published PCT Patent Application Number No. WO2005/118025. This aspect of the invention provides a means of separately adjusting the mass transfer rate and outlet concentrations of two components in the outlet stream from a mass exchange apparatus. Specifically, it provides a means of adjusting oxygen and carbon dioxide mass transfer rates to and from blood and controlling the concentrations of these two dissolved gases in the blood.

It is possible to support life by oxygenating blood passing through a mass exchange apparatus inserted in the patient's blood circulation. Such mass exchange is required when the patient's lungs are ineffective. To date, such life support can be applied in limited circumstances. For example, it is routinely applied during thoracic surgery, when the patient is anaesthetized. It is also applied to patients who are largely immobilized and maintained in hospital intensive care (or similar) units. This aspect of the invention is focused on application to conscious mobile patients.

This aspect of the present invention exploits the fact that, for given liquid and gas phase concentrations, counter-current flow gives higher mass transfer rates than co-current flow. Cross-current flow gives intermediate mass transfer rates. There is described a mixed-flow mass exchange apparatus that can change smoothly through a range of flow patterns. Thus, it can start as a pure co-current flow device. It can be adjusted to a mixed co-current/cross-current device with an increasing proportion of cross flow. Adjustment extends to allow a pure cross-current flow device. Further adjustment allows a mixed cross-current/counter-current device and ultimately a pure counter-current device. Thus, the mixed-flow mass exchange apparatus has a range of adjustment that allows a smooth progression from co-current to counter-current flow. There is a corresponding smooth increase in mass transfer rate. A second adjustment is available in that the total flow rate of one phase (for example, the gas or air phase) can be increased. This increase (by reducing the concentration change across the mass exchanger) also increases mass transfer rates. The two methods of adjusting mass transfer rates impact the mass transfer of individual components differently. In this way, the mass transfer rates of oxygen to blood and carbon dioxide from blood can be adjusted separately.

It is an object of the present invention to provide control of concentrations and mass transfer rates for oxygen and carbon dioxide in mass exchange apparatus for blood oxygenation.

It is a second object of the invention to provide an apparatus that is more generally applicable in mass transfer. Specifically, the device is capable of controlling the concentrations and mass transfer rates of two components without necessarily employing any recycling of air flow.

According to one aspect of the present invention there is provided a mixed-flow mass exchange apparatus for use in mass exchange comprising (a) plural blood flow conduits for defining a blood flow from a blood flow inlet to a blood flow outlet provided thereto; and
(b) plural air flow conduits for defining an air flow from an air flow inlet to an air flow outlet provided thereto;

wherein said plural blood flow conduits and said plural air flow conduits at least partially comprise gas-permeable membrane material, and the conduits are arranged relative to each other such as to enable transfer of carbon dioxide from said blood flow to said air flow and transfer of oxygen from the air flow to the blood flow through said membrane material, and wherein said apparatus additionally comprises an adjuster that enables independent adjustment of the concentration of the carbon dioxide and oxygen in the blood flow.

The mass exchange apparatus herein, comprises plural blood flow conduits for defining a blood flow. That blood flow is from a blood flow inlet to a blood flow outlet provided to the apparatus (e.g. blood flows from a blood flow inlet through the plural blood flow conduits to the blood flow outlet). Embodiments are also envisaged in which plural blood flow inlets and/or blood flow outlets are employed in any suitable arrangement or configuration.

The mass exchange apparatus herein, comprises plural air flow conduits for defining an air flow. That air flow is from an air flow inlet to an air flow outlet provided to the apparatus (e.g. air flows from air flow inlet through the plural air flow conduits to the air flow outlet). Embodiments are also envisaged in which plural air flow inlets and/or air flow outlets are employed in any suitable arrangement or configuration.

The plural blood flow conduits and plural air flow conduits may take the form of tubes or closely-spaced plates.

The plural blood flow conduits and plural air flow conduits at least partially comprise gas-permeable membrane material. The conduits are for example, arranged relative to each other such as to enable transfer, through the membrane material, of oxygen from an air flow to the blood and transfer of carbon dioxide from a blood flow to the air flow.

It will be appreciated that the walls defining the blood flow and air flow conduits may be separately formed and arranged relative to each other to enable the necessary exchange of air (oxygen) and carbon dioxide. In one aspect, the blood flow and air flow conduits share at least some common walls, again with the arrangement selected to enable the necessary exchange of air (oxygen) and carbon dioxide.

Suitably, the blood flow conduits and/or air flow conduits have a diameter (or cross-section of non-circular conduit) and/or spacing of less than 0.5 mm.

Suitably, the adjuster comprises a valve or similar mechanism, which typically acts under the control of a controller in response to sensing by a sensor. In one aspect, the sensor detects the pulse rate of a patient, which indicates patient respiratory demand for oxygen. In other aspects, the sensor detects the breathing rate of the patient and/or the blood circulation rate of the patient, each of which is indicative of the patient respiratory demand for oxygen.

Preferably, the sensor communicates with the controller by suitable communication means. The sensor is typically, an electronic sensor and communication with the controller is typically via wired or wireless electronic transmission means.

The controller suitably acts to control the rate of blood/air mass exchange by separate control of the concentrations of carbon dioxide and oxygen responsive to the sensing of patient respiratory demand by the sensor.

Suitably, the adjuster locates at either the blood flow inlet/outlet or the air flow inlet/outlet.

Suitably, the adjuster comprises an air flow adjuster for adjusting the total flow rate of the air flow. Suitably, the air flow adjuster comprises a valve and/or pump.

Suitably, the adjuster comprises a flow selector for selecting the relative flow pattern of the blood flow and the air flow.

Suitably, the relative flow pattern is selected from the group consisting of co-current flow, counter-current flow, a mixed flow that is partly cross-current and partly co-current and a mixed flow that is partly cross-current and partly counter-current.

Suitably, the flow selector comprises a multi-way valve (e.g. a three-way valve). Alternatively, the flow may comprise a combination of one or more valves and one or more flow restrictors.

Suitably, the multi-way valve permits the proportion of cross-flow either to be infinitely adjustable or alternatively, to be adjustable in small steps.

Embodiments are envisaged in which different flow patterns are mixed and matched to produce combination flow patterns of any suitable type.

In one aspect, an air flow inlet multi-way valve enables separation of the air flow into plural separate air flows for directing to plural separate air flow inlets of the plural air flow conduits.

In another aspect, an air flow outlet multi-way valve enables separation of the air flow into plural separate air flows for directing from plural separate outlets of the plural air flow conduits.

In a further aspect, a blood flow inlet multi-way valve enables separation of the blood flow into plural separate blood flows for directing to plural separate blood flow inlets of the plural blood flow conduits.

In a further aspect, a blood outlet multi-way valve enables separation of the blood flow into plural separate blood flows for directing from plural separate blood flow outlets of the plural blood flow conduits.

According to another aspect of the present invention there is provided the use of the mixed-flow mass exchange apparatus for blood oxygenation so that blood oxygen and carbon dioxide concentrations can be separately controlled.

According to a further aspect of the present invention there is provided of the mixed-flow mass exchange apparatus described above, in which one or both phases are replaced by other fluids and in which one or both of oxygen and carbon dioxide is replaced by other soluble components.

The importance of controlling both oxygen and carbon dioxide concentration in blood has been noted. Specifically, it has been noted that, in membrane mass exchange apparatus, the mass transfer coefficient for carbon dioxide is increased by about an order-of-magnitude more than that of oxygen. Consequently, it is not possible simply to replace a human lung with a membrane mass exchange apparatus. An apparatus is required that enables the blood concentrations of oxygen and carbon dioxide to be controlled separately. The device must also enable higher and lower mass transfer rates to be applied, depending on respiratory demand. These design goals can be met with a mixed-flow mass exchange apparatus.

The requirement to control two concentrations in one stream is unusual in mass exchange. For example, in stripping, scrubbing and distillation, it is normally required to provide maximum enrichment (or depletion) of one component in each exit stream. The concentrations of the non-enriched (or non-depleted) components are a secondary consideration. Standard texts on mass transfer do not give means of accurately controlling two concentration levels in a multi-component stream. See, for example, Coulson J M, Richardson J F, Backhurst J R, and Hunter J H. "Chemical Engineering, Volume 2, Particle Technology and Separation Processes" Butterworth Heinmann 1991, or Perry R H, and Green D W, (eds) "Perry's Chemical Engineers' Handbook" McGraw Hill 1997 [Chapter 5, Knudsen J G, Hottel H C, Sarofim A F, Wankat P C, Knoebel K S, "Heat and Mass Transfer"]. This aspect of the invention shows how such control can be achieved with a mass exchange apparatus for which recycle is not required. Consequently, the invention has wider applications than blood/air mass exchange.

The advantage of a mass exchange apparatus that does not employ recycle is that the mass exchange area can be smaller, and the flow rate through the mass exchange apparatus can be lower. For blood/air mass exchange there is a disadvantage in that the range of transfer rates and concentrations may be less then for recycled systems. It is possible to combine mixed flow and recycle to give a wider range of control options than either technology can achieve on its own.

This aspect of the present invention will now be described further with reference to the accompanying drawings, in which:—

Figure 7:
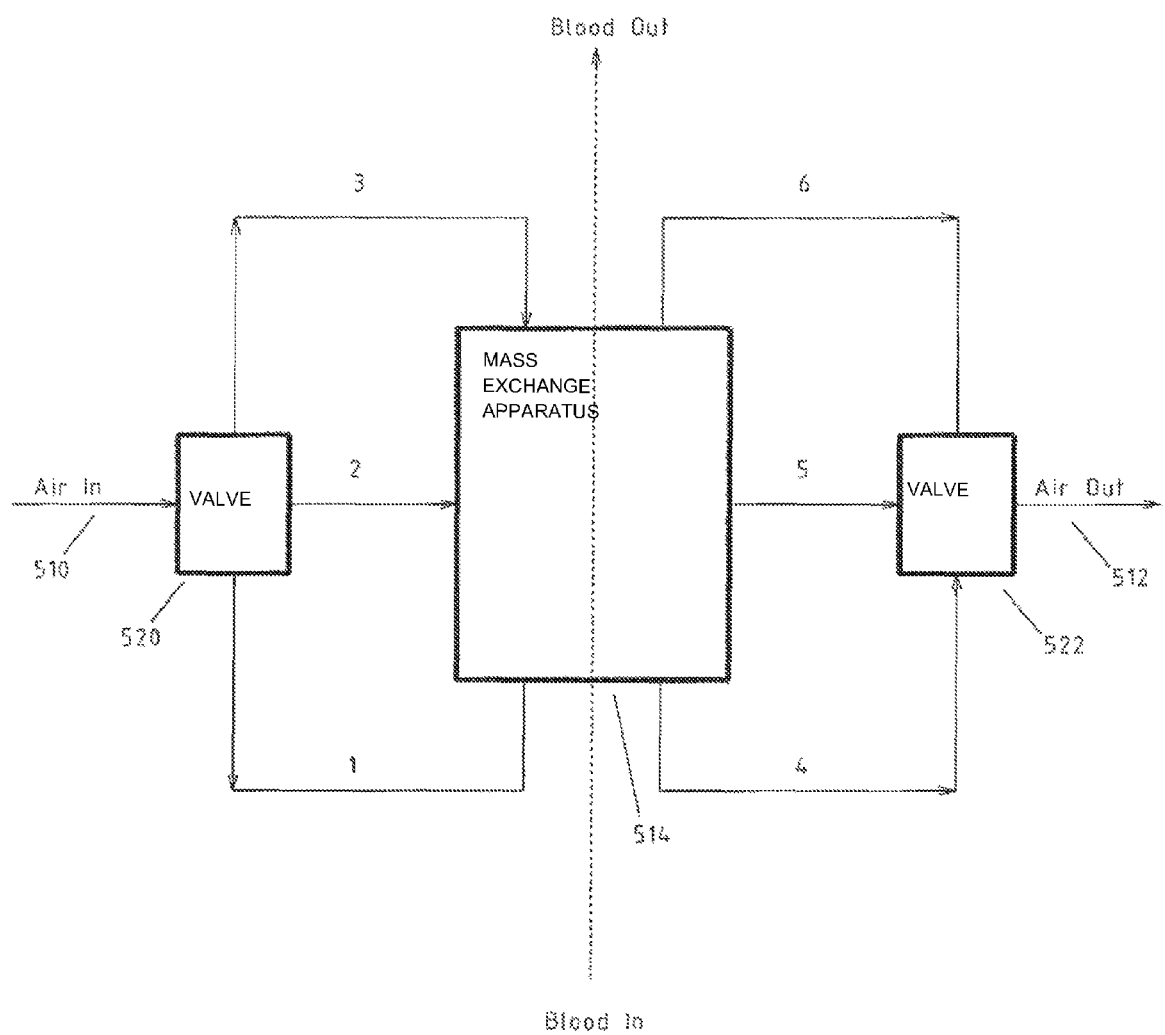
FIG. 7 schematically illustrates a mixed-flow mass exchange apparatus.
Figure 8:
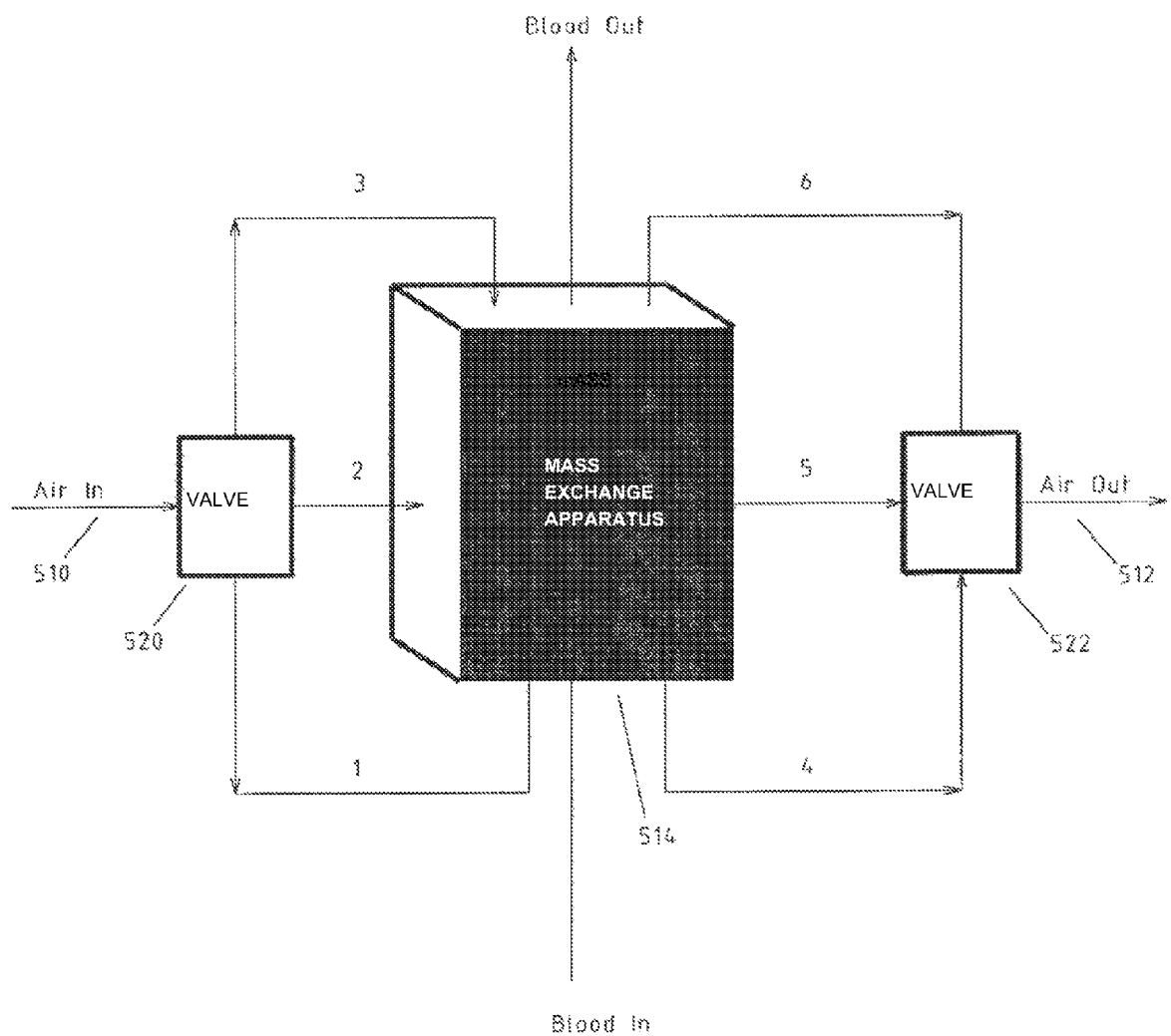
FIG. 8 illustrates a suitable physical form of the mixed-flow mass exchange apparatus of FIG. 7.

FIG. 7 schematically illustrates the mixed-flow mass exchange apparatus; and FIG. 8 illustrates a suitable physical form of the mixed-flow mass exchange apparatus of FIG. 7.

As shown at FIG. 7, the flow of one component is from bottom to top. However, the mass exchange apparatus 514 (e.g. having the detailed form of that mass exchange apparatus of FIG. 1) can operate in any orientation. In illustration, blood comes in the bottom, passes through an array of fine tubes or closely spaced plates, and exits at the top. Air (or an oxygen-containing gas) enters through air inlet 510 and exits at air outlet 512. First multi-way valve 520 is provided to the air inlet 510 and second multi-way valve 522 is provided to the air outlet 512.

In co-current mode, first valve 520 is switched such that the inlet air enters the mass exchange apparatus as stream 1. The first valve 520 closes streams 2 and 3. Second valve 522 is switched such that the outlet gas stream from the exchanger exits as stream 6. Second valve 522 closes stream 4 and 5. Thus, the gas stream enters at the bottom (stream 1) flows concurrently with the liquid stream and exits from the top (stream 6).

In mixed co-current cross-current mode, first valve 520 is switched such that air enters the exchanger through both streams 1 and 2. First valve 520 closes stream 3. Second valve 522 is switched such that air exits the exchanger through both streams 5 and 6. Second valve 522 closes stream 4. Thus, the gas stream flows both up and across the mass exchange apparatus 514. The flow is intermediate between co-current and cross-current. The first and second valves 520, 522 are adjustable allowing a range of flows from 100% co-current to 100% cross-current.

In cross-current mode, first valve 520 is switched such that air enters the exchanger through stream 2. First valve 520 closes streams 1 and 3. Second valve 522 is switched such that air exits through stream 5. Second valve 522 closes streams 4 and 6. The gas flow is then cross-current, namely at right-angles to the liquid flow.

In mixed cross-current counter-current mode, first valve 520 allows flow through steams 2 and 3, and blocks stream 1. Similarly, second valve 522 allows flow through streams 4 and 5, and blocks stream 6. As for mixed co-current cross-current flow, the first and second valves 520, 522 are adjustable to allow a range of flows from 100% cross-current to 100% counter-current.

In counter-current mode, first valve 520 allows flow through stream 3 and no flow through streams 1 and 2. Similarly, second valve 522 allows flow through stream 4 and no flow through streams 5 and 6.

The effectiveness of this mixed-flow mass exchange apparatus approach can be demonstrated by considering the relevant mean driving forces in the different flow modes. We consider the input and output blood and air partial pressures shown in Table 4. The outlet air concentrations correspond to a mean air flow rate approximately 73% of the mean air flow rate in normal respiration.

TABLE 4

Inlet and outlet oxygen and carbon dioxide partial pressures in blood and air.

| | Oxygen (kPa) | | Carbon Dioxide (kPa) | |
|---|---|---|---|---|
| | In | Out | In | Out |
| Air | 21.000 | 14.125 | 0.000 | 5.500 |
| Blood | 5.600 | 11.900 | 6.400 | 5.600 |
| Diff (co-) | 15.400 | 2.225 | 6.400 | 0.100 |
| Mean diff. | | 6.810 | | 1.515 |
| Diff (counter-) | 9.100 | 8.525 | 5.600 | 0.900 |
| Mean diff. | | 8.809 | | 2.571 |

If we assume that partial pressures vary linearly with concentration, the mean driving forces for mass transfer (shown as "Mean diff" in the table) are logarithmic means. Thus, $$\Delta p_{lm} = (\Delta p_1 - \Delta p_2)/\ln(\Delta p_1/\Delta p_2) \quad (4)$$

Even for non-linear variation of partial pressure with concentration, equation (4) gives a good approximation to the relevant mean driving force. Table 4 shows the individual pressure differences as "Diff (co-)" (difference for co-current flow) and "Diff (counter-)" (difference for counter-current flow). We see that, in counter-current flow, the mean driving force for carbon dioxide mass transfer is 70% higher than in co-current flow. Hence, the mass transfer rate would also be approximately 70% higher. The corresponding increase in oxygen mass-transfer rate is approximately 30%.

It has previously been noted that the mass transfer coefficient for carbon dioxide is very high. Hence, with a higher driving force, the blood carbon dioxide concentration will fall until the driving force is again very low. Thus, the carbon dioxide blood partial pressure will be close to the gas-side partial pressure with which it is matched. For co-current flow, the gas-side partial pressure shown in Table 1 is 5.5 kPa. The blood-side partial pressure shown is 5.6 kPa. For counter-current flow, the corresponding gas-side partial pressure is 0 kPa. Thus, the expected blood-side partial pressure will be very low (for example, as low as 0.1 kPa).

The mixed-flow mass exchange apparatus 514 provides a smooth transition both for mass transfer rate and outlet blood carbon dioxide concentration. Thus, the outlet blood carbon dioxide concentration should change smoothly from 5.6 kPa to 0.1 kPa as the mass exchange apparatus 514 changes from co-current to counter-current flow via intermediate mixed-flow patterns.

Oxygen transfer rate and concentration is much less sensitive to flow pattern because larger driving forces are required so that the concentration in the gas phase varies less. However, total mass-transfer rate can be changed by changing the total flow rate of the gas phase.

In summary, this aspect of the invention allows almost any outlet carbon dioxide blood concentration to be selected independent of the oxygen mass-transfer rate.

For applications other than blood/air mass exchange, the mixed flow mass exchange apparatus enables control of two outlet concentrations whenever the mass transfer coefficient of one component differs significantly from that of another. The illustration shows a liquid phase (blood) with a fixed flow direction, and a gas phase (air) with an adjustable flow pattern. For other mass transfer applications, it may be advantageous for the gas phase to flow in a fixed direction and for the liquid phase to have an adjustable flow pattern. The apparatus is also equally applicable to gas/gas and to liquid/liquid mass exchange.

The preferred physical form of the mixed-flow mass-exchange apparatus 514 is a cuboid, as illustrated in FIG. 8. The mass exchange apparatus 514 is shown flattened to give a reasonably long flow path for the gas phase in both horizontal flow and vertical flow. In this way, gas distribution can be improved. For application in blood oxygenation, a flattened cuboid has the additional advantage that the exchanger can be placed against the body of the patient to maintain temperatures close to blood temperature.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A mass exchange apparatus for use in blood/air mass exchange comprising:
    (a) plural blood flow conduits for defining a blood flow from a blood flow inlet provided thereto;
    (b) plural air flow conduits for defining an air flow from an air flow inlet provided thereto;
    (c) plural fluid flow feeds comprising a carbon dioxide feed and either:
        an air feed; or
        an oxygen feed and an inert gas feed;
    (d) a sensor for sensing patient respiratory demand; and
    (e) a controller for controlling the rate of blood/air mass exchange by separate control of the levels of carbon dioxide and oxygen in the air flow responsive to the sensing of patient respiratory demand by the sensor wherein the controller is configured to maintain the partial pressure of carbon dioxide in the air flow above a level of 4 kPa.

2. A mass exchange apparatus according to claim 1, wherein said controller separately controls the level of carbon dioxide and oxygen in the air flow at the air flow inlet.

3. A mass exchange apparatus according to claim 1, additionally comprising a blood flow controller for control of the flow rate of the blood flow.

4. A mass exchange apparatus according to claim 3, wherein said blood flow controller controls the flow rate of the blood flow to be proportional to the blood flow rate through the heart and major veins of a patient.

5. A mass exchange apparatus according to claim 1, wherein the airflow inlet is arranged to receive a fluid flow comprising at least an inert fluid, oxygen and carbon dioxide.

6. A mass exchange apparatus according to claim 5, additionally comprising an air recycle loop, and wherein the airflow inlet receives both a primary air flow feed and a recycled air flow feed from said air recycle loop.

7. A mass exchange apparatus claim 6, wherein the controller acts to control proportions of primary air flow feed and recycled air flow feed received at the air flow inlet.

8. A mass exchange apparatus according to claim 7, wherein the controller acts to control the recycle rate of the air recycle loop.

9. A mass exchange apparatus according to claim 7, wherein the controller acts to control the relative feed rate of the primary air flow feed and recycled air flow feed.

10. A mass exchange apparatus according to claim 5, wherein the air flow inlet receives three fluid flow feeds comprising an inert gas feed, an oxygen feed and a carbon dioxide feed.

11. A mass exchange apparatus according to claim 5, wherein the airflow inlet receives two or three fluid flow feeds, each of which contains one or more of the components oxygen, carbon dioxide and an inert fluid.

12. A mass exchange apparatus according to claim 5, wherein the controller acts to control the relative, proportions of each of the plural fluid flow feeds received at the air flow inlet.

13. A mass exchange apparatus according to claim 12, wherein the controller acts to control the relative flow rates of each of the plural fluid flow feeds received at the air flow inlet.

14. A mass exchange apparatus according to claim 5, additionally containing a secondary mass exchanger to extract carbon dioxide and replenish oxygen in the exhaust from the mass exchange apparatus.

15. A mass exchange apparatus according to claim 1, comprising plural sensors-for sensing patient respiratory demand.

16. A mass exchange apparatus according to claim 15, wherein each of said plural sensors senses a different parameter related to patient respiratory demand.

17. A mass exchange apparatus according to claim 1, wherein the sensor or at least one of the plural sensors senses the pulse rate of a patient.

18. A mass exchange apparatus according to claim 1, wherein the sensor or at least one of the plural sensors senses the breathing rate of a patient.

19. A mass exchange apparatus according to claim 1, wherein the sensor or at least one of the plural sensors senses the blood circulation rate of a patient.

20. A mass exchange apparatus according to claim 1, wherein the sensor or at least one of the plural sensors senses the oxygen concentration in venous blood of a patient.

21. A mass exchange apparatus according to claim 1, wherein the sensor or at least one of the plural sensors senses the strength of the pulse of a patient.

22. A mass exchange apparatus according to claim 1, wherein the sensor or at least one of the plural sensors senses blood oxygen saturation.

23. A mass exchange apparatus according to claim 1, wherein the sensor or at least one of the plural sensors is an electronic sensor and communication with the controller is via wired or wireless electronic transmission means.

24. A mass exchange apparatus according to claim 1, wherein the air flow is arranged to be a combination of air flow that is counter-current to the blood flow and air flow that is co-current to the blood flow.

25. A mass exchange apparatus according to claim 1, wherein the blood flow conduits and/or air flow conduits take the form of tubes or closely-spaced plates.

26. A mass exchange apparatus according to claim 25, wherein the blood flow conduits and/or air flow conduits have a diameter and/or spacing of less than 0.5 millimeters.

27. A mass exchange apparatus according to claim 25, wherein the blood flow conduits and air flow conduits are defined by a series of plates that are separated by a distance of less than 0.5 millimeters.

28. A mass exchange apparatus according to claim 1, wherein the apparatus defines a total mass-exchange area of from 2 to 25 square meters.

29. A mass exchange apparatus according to claim 1, wherein the apparatus defines a total mass-exchange area of from 1 to 5 square meters.

30. An association of plural mass exchange apparatus according to claim 1, wherein said association of apparatus defines a combined mass-transfer area of from 1 to 25 square meters.

31. A respiratory aid apparatus for external connection to a patient comprising
(a) at least one mass exchange apparatus according to claim 1;
(b) an air pump for pumping air through said air conduits to define the air flow; and
(c) a blood pump for pumping blood through said blood conduits to define the blood flow.

32. A respiratory aid apparatus according to claim 31, additionally comprising an air filter for filtering the air.

33. A respiratory aid apparatus according to claim 31, comprising two mass exchange apparatus arranged in parallel fashion.

34. A respiratory aid apparatus according to claim 31, additionally comprising a humidifier for humidifying the air.

35. A respiratory aid apparatus according to claim 31, wherein input tubing to said blood pump is arranged to provide blood extraction and return via a single entry point in a vein of a patient.

36. A respiratory aid apparatus according to claim 35, wherein said input tubing is arranged concentrically.

37. A respiratory aid apparatus according to claim 35, wherein said input tubing comprises two tubes in side-by-side arrangement and received within a third tube of circular cross-section.

38. A respiratory aid apparatus according to claim 31, arranged such that extracted blood undergoes counter-current heat transfer with returned blood.

39. A respiratory aid apparatus according to claim 31, additionally comprising a heat exchange apparatus for preheating the air.

40. A mixed-flow mass exchange apparatus for use in mass exchange comprising;
(a) plural blood flow conduits for defining a blood flow from a blood flow inlet to a blood flow outlet provided thereto; and
(b) plural air flow conduits for defining an air flow from an air flow inlet to an air flow outlet provided thereto;
wherein said plural blood flow conduits and said plural airflow conduits at least partially comprise gas-permeable membrane material, and the conduits are arranged relative to each other such as to enable transfer of carbon dioxide from said blood flow to said air flow and transfer of oxygen from the air flow to the blood flow through said membrane material;
and wherein said apparatus additionally comprises an adjuster that enables independent adjustment of the concentration of the carbon dioxide and oxygen in the blood flow, and wherein the adjuster is configured to maintain the partial pressure of carbon dioxide in the air flow above a level of 4 kPa.

41. A mixed-flow mass exchange apparatus according to claim 40, wherein the adjuster locates at either the blood flow inlet/outlet or the air flow inlet/outlet.

42. A mixed flow mass exchange apparatus according to claim 40, wherein the adjuster comprises an air flow adjuster for adjusting the total flow rate of the air flow.

43. A mixed-flow mass exchange apparatus according to claim 42, wherein said air flow adjuster comprises a valve and/or pump.

44. A mixed flow mass exchange apparatus according to claim 40, wherein the adjuster comprises a flow selector for selecting the relative flow pattern of the blood flow and the airflow.

45. A mixed-flow mass exchange apparatus according to claim 44, wherein the relative flow pattern is selected from the group consisting of co-current flow, counter-current flow, a mixed flow that is partly cross-current and partly co-current and a mixed flow that is partly cross-current and partly counter-current.

46. A mixed flow mass exchange apparatus according to claim 44, wherein said flow selector comprises a multi-way valve.

47. A mixed flow apparatus according to claim 40, wherein the adjuster acts under the control of a controller acting in response to a sensor for sensing patient respiratory demand.

48. A mass exchange apparatus according to claim 47, comprising plural sensors for sensing patient respiratory demand.

49. A mass exchange apparatus according to claim 48, wherein each of said plural sensors senses a different parameter related to patient respiratory demand.

50. A mass exchange apparatus according to claim 47, wherein the sensor or at least one of the plural sensors senses the pulse rate of a patient.

51. A mass exchange apparatus according to claim 47, wherein the sensor or at least one of the plural sensors senses the breathing rate of a patient.

52. A mass exchange apparatus according to claim 47, wherein the sensor or at least one of the plural sensors senses the blood circulation rate of a patient.

53. A mass exchange apparatus according to claim 47, wherein the sensor or at least one of the plural sensors senses the oxygen concentration in venous blood of a patient.

54. A mass exchange apparatus according to claim 47 wherein the sensor or at least one of the plural sensors senses the strength of the pulse of a patient.

55. A mass change apparatus according to claim 47, wherein the sensor or at least one of the plural sensors senses blood oxygen saturation.

56. A mass exchange apparatus according to claim 47, wherein the sensor or at least one of the plural sensors is an electronic sensor and communication with the controller is via wired or wireless electronic transmission means.

57. Use of the mixed-flow mass exchange apparatus of claim 40 for blood oxygenation so that blood oxygen and carbon dioxide concentrations can be separately controlled.

58. A mixed-flow mass exchange apparatus for use in mass exchange comprising:
  (a) plural blood flow conduits for defining a blood flow from a blood flow inlet to a blood flow outlet provided thereto; and
  (b) plural air flow conduits for defining an air flow from an air flow inlet to an air flow outlet provided thereto;
  wherein said plural blood flow conduits and said plural airflow conduits at least partially comprise gas-permeable membrane material, and the conduits are arranged relative to each other such as to enable transfer of carbon dioxide from said blood flow to said air flow and transfer of oxygen from the air flow to the blood flow through said membrane material, and wherein said apparatus additionally comprises an adjuster that enables independent adjustment of the concentration of the carbon dioxide and oxygen in the blood flow;
  wherein the adjuster comprises a flow selector configured to select the relative flow pattern of the blood flow and the air flow;
  wherein said flow selector comprises a multi-way valve;
  wherein an airflow inlet multi-way valve enables separation of the air flow into plural separate airflows for directing to plural separate air flow inlets of the plural airflow conduits.

59. A mixed flow mass apparatus according to claim 58, wherein the adjuster acts under control of a controller in response to sensing of patient respiratory demand by a sensor.

60. A mixed-flow mass exchange apparatus for use in mass exchange comprising;
  (a) plural blood flow conduits for defining a blood flow from a blood flow inlet to a blood flow outlet provided thereto; and
  (b) plural air flow conduits for defining an air flow from an air flow inlet to an air flow outlet provided thereto;
  wherein said plural blood flow conduits and said plural airflow conduits at least partially comprise gas-permeable membrane material, and the conduits are arranged relative to each other such as to enable transfer of carbon dioxide from said blood flow to said air flow and transfer of oxygen from the air flow to the blood flow through said membrane material; and
  wherein said apparatus additionally comprises an adjuster that enables independent adjustment of the concentration of the carbon dioxide and oxygen in the blood flow;
  wherein the adjuster comprises a flow selector configured to select the relative flow pattern of the blood flow and the air flow; and
  wherein said flow selector comprises a multi-way valve;
  wherein an air flow outlet multi-way valve enables separation of the air flow into plural separate air flows for directing from plural separate outlets of the plural air flow conduits.

61. A mixed-flow mass exchange apparatus for use in mass exchange comprising;
  (a) plural blood flow conduits for defining a blood flow from a blood flow inlet to a blood flow outlet provided thereto; and
  (b) plural air flow conduits for defining an air flow from an air flow inlet to an air flow outlet provided thereto;
  wherein said plural blood flow conduits and said plural airflow conduits at least partially comprise gas-permeable membrane material, and the conduits are arranged relative to each other such as to enable transfer of carbon dioxide from said blood flow to said air flow and transfer of oxygen from the air flow to the blood flow through said membrane material;
  and wherein said apparatus additionally comprises an adjuster that enables independent adjustment of the concentration of the carbon dioxide and oxygen in the blood flow;
  wherein the adjuster comprises a multi-way selector valve configured to select the relative flow pattern of the blood flow and the airflow;

wherein a blood flow inlet multi-way valve enables separation of the blood flow into plural separate blood flows for directing to plural separate blood flow inlets of the plural blood flow conduits.

62. A mixed-flow mass exchange apparatus for use in mass exchange comprising;
  (a) plural blood flow conduits for defining a blood flow from a blood flow inlet to a blood flow outlet provided thereto; and
  (b) plural air flow conduits for defining an air flow from an air flow inlet to an air flow outlet provided thereto;
  wherein said plural blood flow conduits and said plural airflow conduits at least partially comprise gas-permeable membrane material, and the conduits are arranged relative to each other such as to enable transfer of carbon dioxide from said blood flow to said air flow and transfer of oxygen from the air flow to the blood flow through said membrane material;
  and wherein said apparatus additionally comprises an adjuster that enables independent adjustment of the concentration of the carbon dioxide and oxygen in the blood flow;
  wherein the adjuster comprises a multi-way selector valve configured to select the relative flow pattern of the blood flow and the airflow;
  wherein a blood outlet multi-way valve enables separation of the blood flow into plural separate blood flows for directing from plural separate blood flow outlets of the plural blood flow conduits.

\* \* \* \* \*